(12) United States Patent
Albalos et al.

(10) Patent No.: US 8,399,194 B2
(45) Date of Patent: Mar. 19, 2013

(54) HETEROPOLYNUCLEOTIDE DUPLEXES WITH PURINE—PURINE BASE PAIRING

(75) Inventors: Maria Albalos, Hercules, CA (US); Thomas Battersby, El Cerrito, CA (US); Edward Brooks, Richmond, CA (US); Michel Friesenhahn, Albany, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 606 days.

(21) Appl. No.: 12/521,012

(22) PCT Filed: Dec. 21, 2007

(86) PCT No.: PCT/US2007/088617
§ 371 (c)(1),
(2), (4) Date: Feb. 23, 2010

(87) PCT Pub. No.: WO2008/083090
PCT Pub. Date: Jul. 10, 2008

(65) Prior Publication Data
US 2010/0190972 A1    Jul. 29, 2010

Related U.S. Application Data

(60) Provisional application No. 60/871,891, filed on Dec. 26, 2006.

(51) Int. Cl.
*C12Q 1/68* (2006.01)
(52) U.S. Cl. .......................... 435/6.11; 435/6.1
(58) Field of Classification Search .................. None
See application file for complete search history.

(56) References Cited

FOREIGN PATENT DOCUMENTS

WO    2006095981    9/2006

OTHER PUBLICATIONS

Novelli G et al: "Inosine—containing primers in human *papillomavirus* detection by polymerase chain reaction", Biomedical and Pharmacontherapy, 46: 4, pp. 167-169, (1992).
Li Ying et al: Oligonucleotides containing G cntdot A pairs: Effect of flanking sequences on structure and stability! Biochemistry, 34: 31, pp. 10056-10062, (1995).
Kypr Jaroslav et al: "DNA homoduplexes containing no pyrimidine nucleotide" European Biophysics Journal, 32: 2, , pp. 154-158, (2003).
Battersby et al: "An unusual Mode of DNA Duplex Association: Watson-Crick Interaction of All-Purine Deoxyribonucleis Acids" Chemistry and Biology, Current Biology, 14: 5, pp. 525-531, (2007).
Abraham Michelle L et al: "Nucleobase analogs for degenerate hybridization devised through confomational pairing analysis" Biotechniques, 43: 5, pp. 617-618, 620, 62 (2007).
Groebke et al., "Why Pentose- and Not Hexose-Nucleic Acids? Purine-Purine Pairing in homo-DNA: Guanine, Isoguanine, 2,6-Diaminopurine and Xanthine," Helvetica Chimca Acta, 81:375-474 (1998), Abstract Only.
Arnez and Seitz, "DNA Made of Purines Only," Chemistry and Biology, 14:467-469 (2007).
Evertsz et al., "Parallel-stranded duplex DNA containing blocks of trans purine-purine and purine-pyrimidine base pairs," Nucleic Acids Research, 22(16): 3293-3303 (1994).
International Search Report for WO 2008/083090, (Nov. 19, 2008).

*Primary Examiner* — James Martinell

(57) ABSTRACT

The present invention relates to stable anti-parallel heteropolynucleotide duplexes, comprising a plurality of complementary purine-purine nucleobase dyads, wherein the nucleobase is coupled to a pentose sugar backbone. The present invention further relates to methods of hybridizing two heteropolynucleotide molecules to form such purine-purine nucleobase dyads, as well as kits and solid supports comprising such purine-purine nucleobase dyads.

19 Claims, 11 Drawing Sheets

A·H            G·J

SEQUENCE LISTING

<160> NUMBER OF SEQ ID NOS: 16

<210> SEQ ID NO 1
<211> LENGTH: 13
<212> TYPE: DNA
<213> ORGANISM: Homo sapiens

<400> SEQUENCE: 1
acgactttgt gcg                                                          13

<210> SEQ ID NO 2
<211> LENGTH: 13
<212> TYPE: DNA
<213> ORGANISM: Homo sapiens

<400> SEQUENCE: 2
cgcacaaagt cgt                                                          13

<210> SEQ ID NO 3
<211> LENGTH: 13
<212> TYPE: DNA
<213> ORGANISM: Homo sapiens

<400> SEQUENCE: 3
acgactttgt gcg                                                          13

<210> SEQ ID NO 4
<211> LENGTH: 13
<212> TYPE: DNA
<213> ORGANISM: Homo sapiens

```
<400> SEQUENCE: 4
cgcacaaagt cgt                                              13

<210> SEQ ID NO 5
<211> LENGTH: 14
<212> TYPE: DNA
<213> ORGANISM: Homo sapiens

<400> SEQUENCE: 5
gggagaaagh gghg                                             14

<210> SEQ ID NO 6
<211> LENGTH: 14
<212> TYPE: DNA
<213> ORGANISM: Homo sapiens

<400> SEQUENCE: 6
gaggaghhhg hggg                                             14

<210> SEQ ID NO 7
<211> LENGTH: 14
<212> TYPE: DNA
<213> ORGANISM: Homo sapiens

<400> SEQUENCE: 7
aaagaaggga gaag                                             14

<210> SEQ ID NO 8
<211> LENGTH: 14
<212> TYPE: DNA
<213> ORGANISM: Homo sapiens

<400> SEQUENCE: 8
gggagaaagh gghg                                             14

<210> SEQ ID NO 9
<211> LENGTH: 14
<212> TYPE: DNA
<213> ORGANISM: Homo sapiens

<400> SEQUENCE: 9
gggagaaagh gghg                                             14

<210> SEQ ID NO 10
<211> LENGTH: 14
<212> TYPE: DNA
<213> ORGANISM: Homo sapiens

<400> SEQUENCE: 10
gghahaaahh gghg                                             14

<210> SEQ ID NO 11
<211> LENGTH: 15
<212> TYPE: DNA
<213> ORGANISM: Homo sapiens

<400> SEQUENCE: 11
cccccttctc tccct                                            15

<210> SEQ ID NO 12
<211> LENGTH: 14
<212> TYPE: DNA
<213> ORGANISM: Homo sapiens
```

```
<400> SEQUENCE: 12
cggagaaagt cgtg                                                14

<210> SEQ ID NO 13
<211> LENGTH: 14
<212> TYPE: DNA
<213> ORGANISM: Homo sapiens

<400> SEQUENCE: 13
cacgactttc tccg                                                14

<210> SEQ ID NO 14
<211> LENGTH: 15
<212> TYPE: DNA
<213> ORGANISM: Homo sapiens

<400> SEQUENCE: 14
gaggagtttc tccct                                               15

<210> SEQ ID NO 15
<211> LENGTH: 14
<212> TYPE: DNA
<213> ORGANISM: Homo sapiens

<400> SEQUENCE: 15
cggagaaagt cgtg                                                14

<210> SEQ ID NO 16
<211> LENGTH: 14
<212> TYPE: DNA
<213> ORGANISM: Homo sapiens

<400> SEQUENCE: 16
gaggaggggg gggg                                                14
```

HETEROPOLYNUCLEOTIDE DUPLEXES WITH PURINE—PURINE BASE PAIRING

CROSS REFERENCE TO RELATED APPLICATION

This application claims the benefit under 35 U.S.C. §119(e) of U.S. Provisional Patent Application No. 60/871,891, filed Dec. 26, 2006, the disclosure of which is incorporated, in its entirety, by this reference.

TECHNICAL FIELD OF THE INVENTION

The present invention relates generally to the field of nucleic acids, and more particularly to purine-purine oligonucleotides and methods of using the same.

BACKGROUND OF THE INVENTION

DNA and RNA constitute the key molecular components of all genetic processes, and have similar structural components. DNA typically exists as a complex of two anti-parallel linear strands or sequences of deoxyribonucleotide structural units, each unit of which consists of a nitrogenous base (adenine (A), thymidine (T), cytosine (C) or guanine (G)), a pentose sugar (a 5-carbon sugar), and a phosphate group. RNA is typically single stranded, and uses uracil (U) in place of thymidine (T). Moreover, the pentose sugar in DNA is 2-deoxyribose, while the pentose sugar in RNA is ribose. The nitrogenous bases of DNA and RNA are of two classes: the larger nine-member double-ring purines, A an G, and smaller six-member single-ring pyrimidines, C, T and U.

According to the Watson-Crick paradigm, a double helix is formed from two strands of DNA, which are paired by hydrogen bonding between complementary nitrogenous base pairs. The rules of base pairing require size complementarity—large purines pair with small pyrimidines. A further basis of complementarity is the geometrical (or spatial) correspondence of hydrogen bond donors and acceptors present on the nitrogenous bases: The G-C pair has three hydrogen bonds that pair, and the A-T base pair has two hydrogen bonds that pair, in such a manner that hydrogen bond donors pair with hydrogen bond acceptors. Other possible base pairings are said to be "mismatched". "Mismatches" between nucleotide bases result in greater instability relative to perfectly matched nucleotide bases. Instability caused by nucleotide base mismatches can be detected by means of comparing melting (disassociation) temperatures of hybridized DNA strands, and is the current basis of many forms of genetic testing.

Alternative base pairing systems utilizing only purine nucleobases have been investigated. For example, although a duplex from polyinosine and polyadenosine oligonucleotides through Watson-Crick interaction of inosine and adenosine (two purine nucleobases) has previously been reported (Rich, Nature 181, 521-525 (1958)), subsequent studies showed that the complex was actually a triplex with no independent Watson-Crick duplex present. (Howard et al., Biochemistry, 16, 4647-4650 (1977). Another study describes weak interaction between polyinosine and a substituted polyadenosine, and speculates that more than one mode of interaction was likely present, including possibly duplex formation through Watson-Crick interaction, although the data was inconclusive. (Howard et al., Biochemistry, 16, 4637-4646 (1977). Another study described duplexes formed through interaction of purine-purine dyads based on non-natural backbones with modified non-ribosyl sugars (homo-DNA, consisting of hexopyranosyl-(6'→4')-oligonucleotides); the authors further stated that duplex formation is not possible in purine-purine duplexes having natural backbones (Groebke et al., Helvetic Chimica Acta, Vol. 81, 1998). Non-Watson-Crick pairing all-purine duplexes with repeating sequences have also been reported. (Howard et al., J. Biol. Chem. 250, 3951-3959 (1975)) (Howard et al., Biochemistry, 16, 4637-4646 (1977)).

More recently, formation of duplexes with a natural ribosyl backbone pairing purines with unnatural nucleobases and pyrimidines with additional unnatural nucleobases has been reported (Gao et al., Angew. Chem. Int. Ed. 44, 3118-3122 (2005).

Notwithstanding the failure in the prior art to generate oligonucleotides comprising purine-purine dyads, purine-purine duplexes could potentially be useful for hybridization in nucleic acid-based diagnostic assays. For example, nucleic acid sequences containing a plurality of purine-purine regions could be enzymatically amplified and targeted by purine-purine probes. Polypurine regions of nucleic acid sequence could be replicated by natural polymerases pairing pyrimidines with purines to yield complementary polypyrimidine sequences, and could also be specifically targeted for hybridization with completely different complementary all-purine sequences. In addition, purine-purine duplexes could be used in situations where canonical Watson-Crick duplexes may be affected by common processes of molecular biology. Duplexes of purine-purine nucleic acids will not act as substrates in many enzymatically-mediated processes, such as polymerase replication and amplification, ligation, restriction, and mismatch repair, which depend on recognition of a duplex nucleic acid. For example, oligonucleotides with capture sequences complementary to oligonucleotides immobilized on a surface could be used to form all-purine duplex structures, which would be inert in the presence of these enzymatically-mediated processes. Small molecules that target duplex nucleic acids could also exhibit altered interaction with purine-purine duplexes, thereby allowing, for example, dyes such as SYBR Green I to be used to specifically detect formation of a canonical duplex in solution with purine-purine duplexes performing a hybridization function that remains undetectable in monitoring fluorescence of the dye.

Accordingly, there is a need in the art for nucleotide duplexes comprising complementary purine-purine nucleobases.

SUMMARY OF THE INVENTION

The present invention is generally directed to stable anti-parallel heteropolynucleotide duplexes comprising a plurality of complementary purine-purine nucleobase dyads that hybridize through Watson-Crick interactions and methods of preparing such sequences.

In some embodiments, the duplexes of the invention are in the form of a stable anti-parallel heteropolynucleotide duplex comprising a plurality of complementary purine-purine nucleobase dyads, wherein the nucleobase is coupled to a pentose sugar backbone. In some embodiments, the duplexes consist essentially of a plurality of purine-purine dyads, wherein the nucleobase is coupled to a pentose sugar backbone. In some embodiments, the pentose sugar is selected from D-ribose and 2'-deoxy-D-ribose. In some embodiments, a plurality of the purine-purine nucleobase dyads form complementary Watson-Crick interactions. In other embodiments, the nucleic acid duplex may also comprise a plurality of complementary canonical Watson-Crick paired purine-pyrimidine nucleobase dyads.

In yet other embodiments, the purine-purine nucleobase dyads form Watson-Crick interactions, and at least one purine-purine nucleobase dyad comprises a purine that adopts a tautomer that is not the major species of the nucleobase present in aqueous solution in the absence of this interaction. In other embodiments, the purine-purine nucleobase dyads form Watson-Crick interactions, and both purines of at least one purine-purine dyad adopt a tautomer that is not the major species of the nucleobase present in aqueous solution in the absence of this interaction.

In other embodiments, the purine-purine nucleobase dyads are selected from the following:

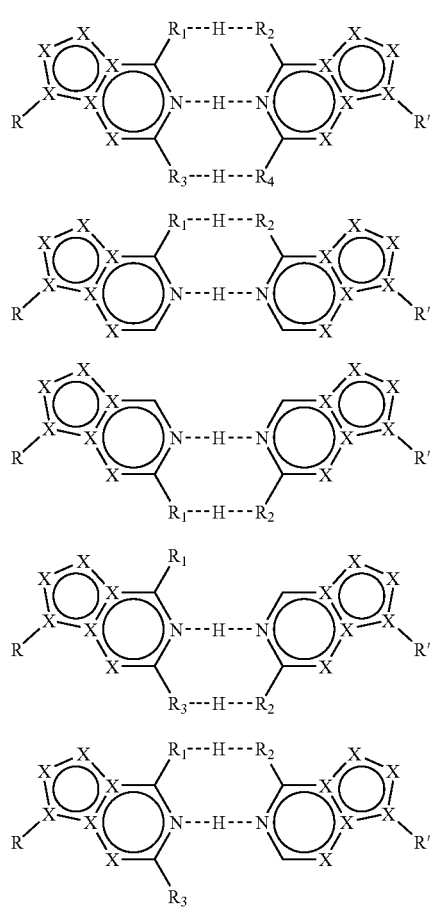

wherein X is independently selected from the group consisting of C, N, CH, and NH, provided that aromaticity is preserved;
each R and R' is selected from the group consisting of ribose and deoxyribose; and
each $R_1$, $R_2$, $R_3$, and $R_4$ is selected from the group consisting of hydrogen bond donors —$NH_2$, —SH, and —OH, or the group of hydrogen bond acceptors =O, =S, =NH, —OH, —SH, and —$NH_2$, such that an individual hydrogen atom within a hydrogen bond is associated with one donor and one acceptor.

In still other embodiments, a plurality of the purine-purine nucleobase dyads have a hydrogen bond donor:acceptor pattern selected from the following:

| | | |
|---|---|---|
| puADD-puDAA | puAD_-puDAA | puAD_-puDA_ |
| puAAD-puDDA | puAA_-puDDA | puAA_-puDD_ |

-continued

| | | |
|---|---|---|
| puADA-puDAD | puADA-pu_AD | pu_DA-pu_AD |
| | puADD-pu_AA | pu_DD-pu_AA |
| | puAAD-pu_DA | pu_AD-pu_DA |
| | puADA-puDA_ | puAD_-puDA_ |

In still other embodiments, one or more purine-purine nucleobase dyad consists of: (a) a first purine selected from adenine, 7-deazaadenine, or 3-deazaadenine, and (b) a second purine selected from hypoxanthine, 7-deazahypoxanthine, 3-deazahypoxanthine, 7-deazaxanthine, or xanthine. In other embodiments, one or more purine-purine nucleobase dyad consists of (a) a first purine selected from guanine, 7-deazaguanine, or 3-deazaguanine and (b) a second purine that is isoguanine.

In another embodiment, a plurality of purine-purine nucleobase dyads are contiguous. In some embodiments, the nucleic acid duplex comprises at least 3 contiguous purine-purine nucleobase dyads. In some embodiments, the nucleic acid duplex comprises at least 4 contiguous purine-purine nucleobase dyads. In some embodiments, the nucleic acid duplex comprises 5 or more contiguous purine-purine nucleobase dyads. In some embodiments, the nucleic acid duplex comprises a plurality of complementary purine-pyrimidine nucleobase dyads.

In another embodiment, the nucleic acid duplex comprises a detectable label bound to at least one of the nucleobases. The detectable label may be a fluorophore. The nucleic acid duplex may also comprise a quencher.

In another aspect, the invention includes methods for making the above heteropolynucleotide duplexes. In particular embodiments, the methods described below may utilize any of the purine-purine duplexes described in the above paragraphs. In one embodiment, the invention includes a method for hybridizing two nucleic acid molecules, comprising:
    providing a heteropolynucleotide template comprising a region having a plurality of purine nucleotides coupled to a backbone of ribose or deoxyribose, and phosphate;
    hybridizing to the heteropolynucleotide template an oligonucleotide molecule comprising a plurality of purine nucleotides coupled to a backbone of ribose or deoxyribose, and phosphate,
    wherein a plurality of the purine nucleotides of the oligonucleotide molecule hybridize to purine nucleotides of the heteropolynucleotide template, thereby forming a stable anti-parallel heteropolynucleotide duplex having a plurality of purine-purine dyads.

In another embodiment, the invention includes a method for detecting the presence or absence of a polymorphism in a polynucleotide molecule, comprising:
    providing a heteropolynucleotide template comprising a region consisting of a plurality of purine nucleotides coupled to a backbone consisting of ribose or deoxyribose, and phosphate, wherein the region of purine nucleotides includes one or more nucleotides characterized by polymorphic variations;
    hybridizing to the heteropolynucleotide template an oligonucleotide molecule comprising a plurality of purine nucleotides coupled to a backbone consisting of ribose or deoxyribose, and phosphate,
    wherein a plurality of the purine nucleotides of the oligonucleotide molecule are complementary to purine nucleotides of the heteropolynucleotide template having one of the polymorphic variations, thereby forming a stable anti-parallel heteropolynucleotide duplex.

In another aspect, the present invention includes kits comprising an oligonucleotide molecule comprising a plurality of purine nucleotides coupled to a backbone consisting of ribose or deoxyribose, and phosphate, wherein a plurality of the purine nucleotides of the oligonucleotide molecule are complementary to purine nucleotides of a heteropolynucleotide template. In some embodiments, the kit may comprise an oligonucleotide molecule comprising one or more regions consisting of a plurality of contiguous purine nucleotides coupled to a backbone consisting of ribose or deoxyribose, and phosphate, wherein a plurality of the purine nucleotides of the oligonucleotide molecule are complementary to contiguous purine nucleotides coupled to a backbone consisting of ribose or deoxyribose, and phosphate of a heteropolynucleotide template.

In another aspect, the present invention includes chips comprising an oligonucleotide molecule comprising a plurality of purine nucleotides coupled to a backbone consisting of ribose or deoxyribose, and phosphate, wherein the purine nucleotides of the oligonucleotide molecule are complementary to a plurality of purine nucleotides of a heteropolynucleotide template. The chips may also comprise oligonucleotides molecules comprising one or more regions consisting of a plurality of contiguous purine nucleotides coupled to a backbone consisting of ribose or deoxyribose, and phosphate, wherein a plurality of the purine nucleotides of the oligonucleotide molecule are complementary to contiguous purine nucleotides coupled to a backbone consisting of ribose or deoxyribose, and phosphate of a heteropolynucleotide template.

BRIEF DESCRIPTION OF THE DRAWINGS

FIGS. 8a and 8b show only a slight shift away from the N1-H tautomer with increasing temperature.

DETAILED DESCRIPTION OF THE INVENTION

Figure 1:
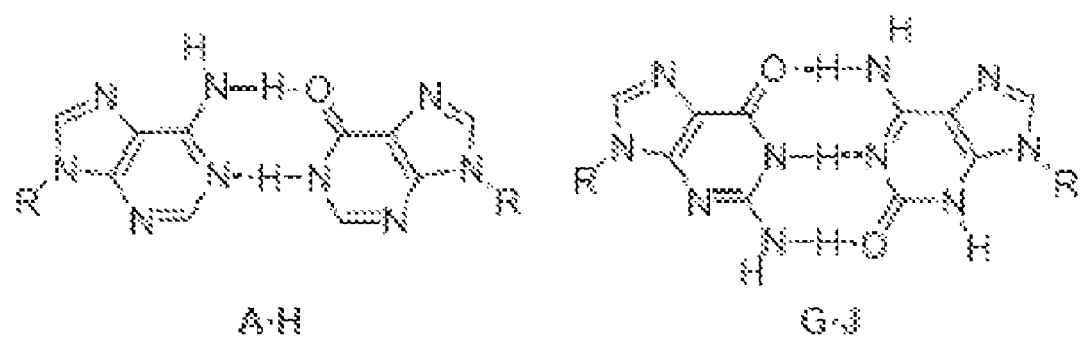
FIG. 1 is a depiction of Watson-Crick, purine-purine pairing of adenine with hypoxanthine, and guanine with isoguanine.

Unless defined otherwise, technical and scientific terms used herein have the same meaning as commonly understood by one of ordinary skill in the art to which this invention pertains. Units, prefixes, and symbols may be denoted in their SI accepted form. Unless otherwise indicated, nucleic acid sequences are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic acid sequence discrepancy within the application, the figures control. One skilled in the art will recognize many methods and materials similar or equivalent to those described herein, which could be used in the practice of the present invention. The present invention is in no way limited to the methods and materials described herein, and it is understood that other embodiments of the invention may exist that are not expressly described herein. For purposes of the present invention, the following terms are defined below.

The term "purine-purine Watson-Crick interaction" as used herein means the interaction of two purine nucleobases joined through hydrogen bonding in which the N-1 nitrogen atoms of the purines are directly opposite each other, the functional groups at C-2 (if present) on each purine are directly opposite each other, and the functional groups at C-6 (if present) on each purine are directly opposite each other.

The term "nucleobase" as used herein means any nitrogen-containing heterocyclic moiety capable of forming Watson-Crick-type hydrogen bonds and stacking interactions in pairing with a complementary nucleobase or nucleobase analog (i.e., derivatives of nucleobases) when that nucleobase is incorporated into a polymeric structure. "Heterocyclic" refers to a molecule with a ring system in which one or more ring atom is a heteroatom, e.g., nitrogen, oxygen, or sulfur (i.e., not carbon), such as a purine, pyrimidine, or analog thereof.

A large number of nucleobases, nucleobase analogs and nucleobase derivatives are known. Non-limiting examples of nucleobases include purines and pyrimidines, and modified forms, e.g., 7-deazapurine. Typical nucleobases are the naturally occurring nucleobases adenine, guanine, cytosine, uracil, thymine, and analogs (Seela, U.S. Pat. No. 5,446,139) of the naturally occurring nucleobases, e.g., 7-deazaadenine, 7-deazaguanine, 7-deaza-8-azaguanine, 7-deaza-8-azaadenine, inosine, nebularine, nitropyrrole (Bergstrom, J. Amer. Chem. Soc., 117:1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, O-6-methylguanine, N-6-methyladenine, O-4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "nucleoside" as used herein means a nucleobase linked to a carbohydrate. Nucleosides are coupled to D-ribose (in RNA) or 2'-deoxy-D-ribose (in DNA) carbohydrate through an N-glycosidic bond between the anomeric carbon of the carbohydrate (1'-carbon atom of the carbohydrate) and the nucleobase. When the nucleobase is purine, e.g., A or G, the ribose sugar is generally attached to the N9-position of the nucleobase. When the nucleobase is pyrimidine, e.g., C, T or U, the sugar is generally attached to the N1-position of the nucleobase. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Ribose examples include ribose, 2'-deoxyribose, 2', 3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., Nucl. Acids Res., 19:4067-74 [1991]), 2'-4'- and 3'-4'-linked and other "locked" or "LNA", bicyclic sugar modifications (WO 98/22489; WO 98/39352; WO 99/14226).

Carbohydrates (also called sugars) can include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi et al., Nucl. Acids Res., 21:4159-4165 (1993); Fujimori, J. Amer. Chem. Soc., 112:7435 (1990); Urata, (1993) Nucleic Acids Symposium Ser. No. 29:69-70).

The term "nucleotide" as used herein means a nucleoside in a phosphorylated form—a phosphate ester of a nucleoside, as a monomer unit or within a polynucleotide polymer. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygen moieties, e.g., α-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry, see Shabarova, Z. and Bogdanov, A. Advanced Organic Chemistry of Nucleic Acids, VCH, New York, 1994. The term "nucleic acid" as used herein means a nucleobase polymer having a backbone formed from nucleotides, or nucleotide analogs. "Nucleic acid" and "polynucleotide" are considered to be equivalent and interchangeable. Nucleic acids are commonly in the form of DNA or RNA.

The term "nucleic acid" includes polynucleotides of genomic DNA or RNA, cDNA, semisynthetic, or synthetic origin. Nucleic acids may also substitute standard nucleotide bases with nucleotide isoform analogs, including, but not limited to iso-C and iso-G bases, which may hybridize more or less permissibly than standard bases, and which will preferentially hybridize with complementary isoform analog bases. Many such isoform bases are described, for example, by Benner et al., (1987) Cold Spring Harb. Symp. Quant. Biol. 52, 53-63. In representations of degenerate primers or mixture of different strands having mutations in one or several positions, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide.

"Polynucleotide" and "oligonucleotides" are used interchangeably and mean single-stranded and double-stranded polymers of nucleotide monomers, including 2'-deoxyribonucleotides (DNA) and ribonucleotides (RNA) linked by internucleotide phosphodiester bond linkages, (e.g., 3'-5', and 2'-5'), inverted internucleotide phosphodiester bond linkages (e.g., 3'-3' and 5'-5') branched structures, or internucleotide analogs. A "polynucleotide sequence" refers to the sequence of nucleotide monomers along the polymer. "Polynucleotides" are not limited to any particular length of nucleotide sequence, as the term "polynucleotides" encompasses polymeric forms of nucleotides of any length. Polynucleotides that range in size from about 5 to about 40 monomeric units are typically referred to in the art as oligonucleotides. Polynucleotides that are several thousands or more monomeric nucleotide units in length are typically referred to as nucleic acids. Polynucleotides can be linear, branched linear, or circular molecules. Polynucleotides also have associated counter ions, such as H+, NH4+, trialkylammonium, Mg2+, Na+ and the like.

Polynucleotides that are formed by 3'-5' phosphodiester linkages are said to have 5'-ends and 3'-ends because the mononucleotides that are reacted to make the polynucleotide are joined in such a manner that the 5' phosphate of one mononucleotide pentose ring is attached to the 3' oxygen (i.e., hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand.

A polynucleotide may be composed entirely of deoxyribonucleotides, entirely of ribonucleotides, or chimeric mixtures thereof. Polynucleotides may be composed of internucleotide nucleobase and sugar analogs. Unless denoted otherwise, whenever a polynucleotide sequence is represented, it will be understood that the nucleotides are in 5' to 3' orientation from left to right.

The term "heteropolynucleotide" means a polynucleotide comprising more than one nucleobase type.

The term "duplex" means a bimolecular nucleic acid complex, usually formed through association of a series of interacting nucleobase dyads, one from each molecule of the complex. A single nucleic acid molecule may also have regions of duplex association by folding back onto itself and intramolecularly hybridizing to a complementary sequence.

The term "complementary" means that two nucleobases are capable of associating in a Watson-Crick interaction of potential hydrogen bonding functionality without repulsive interaction(s). "Complementary" also means that a nucleobase of a polynucleotide is capable of hybridizing to a corresponding nucleobase in a different polynucleotide. As used herein, the term "complementary" is not limited to canonical Watson-Crick base pairs with A/T, G/C and U/A. Thus, nucleobase pairs may be considered to be "complementary" if one or both of the nucleobases is a nucleobase other than A, G, C, or T. The term "complementary" also refers to antiparallel strands of polynucleotides (as opposed to a single nucleobase pair) that are capable of hybridizing. The term "complementary" as used in reference to two nucleotide sequences or two nucleobases, implies that the nucleotides sequences or nucleobases are "corresponding."

The term "comprising" means the listed elements, plus any additional unspecified elements.

The term "consisting essentially of" means the listed elements, plus any additional unspecified elements that do not function as a nucleobase dyad. Thus, with respect to claims reciting polynucleotide duplexes "consisting essentially of" a plurality of complementary purine-purine nucleobase dyads, the term "consisting essentially of" is used to characterize only the nucleobase dyads, and thus the claim is open to the inclusion of other elements that are not nucleobase dyads, such as pentose sugar backbones, phosphate groups, detectable labels, and cross-linking agents, etc.

The term "corresponding" when used to refer to two nucleotide sequences or two nucleobases within a sequence means having the same or nearly the same relationship with respect to position and complementarity, or having the same or nearly the same relationship with respect to structure, function, or genetic coding (for example, as between a gene and the "corresponding" protein encoded by the gene). For example, a nucleotide sequence "corresponds" to a region of a polynucleotide template if the two sequences are complementary or have portions that are complementary. Similarly, a nucleobase of an oligomer "corresponds" to a nucleobase of a polynucleotide template when the two nucleobases occupy positions such that when the oligomer and the polynucleotide hybridize the two nucleobases pair opposite each other. The term "corresponding" is generally used herein in reference to the positional relationship between two polynucleotide sequences or two nucleobases. The term "corresponding" does not imply complementarity; thus, corresponding nucleobases may be complementary, or may be non-complementary.

The term "dyad" means two nucleobases or analogs paired within a duplex, one from each opposing strand of the duplex.

The term "backbone" means a repeating linear polymer to which nucleobases or analogs are attached. In DNA the backbone is formed by alternating 2'-deoxy-D-ribose and phosphate units. In RNA the backbone is formed by alternating D-ribose and phosphate units.

The phrase "hydrogen bonding pattern" means the hydrogen bonding pattern of acceptor (A) and donor (D) groups of a pyrimidine or pyrimidine analog (py) and a purine or purine analog (pu) molecule, designated using the nomenclature of Benner (Lutz, et al. Differential discrimination of DNA polymerases for variants of the non-standard nucleobase pair between xanthosine and 2,4-diaminopyrimidine, two components of an expanded genetic alphabet, Nucleic Acids Res. 24:1308-1313 (1996)). The term "pu" as used herein denotes a carbon/nitrogen heterocycle isosteric to the ring system of purines (i.e., adenine and guanine) with a nitrogen atom at position 1. Functionality capable of acting as hydrogen bond donors or acceptors in Watson-Crick interaction may be present at the carbon atoms of positions 2 and 6. The nature of this functionality, if present, is indicated by a series of three symbols representing positions moving around the pu ring from position 6 to position 1 to position 2 ("D"=H bond donor, "A"=H bond acceptor, "_"=no functionality).

The hydrogen bonding patterns of the natural purines are denoted as puDA_ (adenine) and puADD (guanine). Similarly, the hydrogen bonding patterns of the natural pyrimidines are pyDAA (cytosine) and pyADA (thymine/uracil). Thus, the notation representing cytosine-guanine bonding pattern is pyDAA-puADD, and the thymine/uracil-adenine bonding pattern is pyADA-puDA_.

The term "ribose" as used herein means a pentose sugar of the general formula C5H10O5 occurring as a component of riboflavin, nucleotides, and nucleic acids.

The term "deoxyribose" as used herein means any of certain pentose carbohydrates derived from ribose by the replacement of a hydroxyl group with a hydrogen atom of the general formula C5H10O4.

The term "phosphate" as used herein means a salt or ester of phosphoric acid.

The abbreviation "Tm" as used herein means the "melting temperature." The melting temperature is the temperature at which half of a population of double-stranded polynucleotide molecules or nucleobase oligomers, in homoduplexes or heteroduplexes, become dissociated into single strands. The Tm of a double-stranded nucleobase oligomeric molecule is influenced by the types of bases, the base sequence, structure of the oligomeric linkages, and the presence of non-natural features in the sequence, such as artificial linkages. Methods for calculating or experimentally determining Tm are known in the art. See, for example, Breslauer et al. Proc. Natl. Acad. Sci. USA 83: 3746-3750 (1986); Baldino et al. Methods in Enzymol. 168: 761-777 (1989); and Breslauer Methods in Enzymol. 259: 221-242 (1995).

The term "antiparallel" is used to refer to interaction in which an oligonucleotide strand oriented in the 5'-3' direction is hybridized to a complementary strand oriented in the 3'-5' direction.

The term "stable," as used in reference to a heteropolynucleotide duplex, means that the duplex remains hybridized essentially exclusively in the form of a duplex under typical salt and temperature conditions used in nucleic acid diagnostic applications.

The practice of the present invention will employ, unless otherwise indicated, conventional techniques of molecular biology, microbiology, recombinant DNA techniques, and oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

In accordance with the present invention, purine-purine nucleic acid duplexes associating through Watson-Crick pairing have been constructed and characterized. Contrary to current paradigms, antiparallel deoxyribose duplexes can be formed through association of purines found in natural ribonucleosides. The purine-purine nucleic acid duplexes can include a N3-H tautomer of isoguanine Sequence-specific recognition displayed by these structures can enable the duplexes to be suitable for information storage and replication by a mechanism analogous to the genetic system. The antiparallel deoxyribose duplexes lack pyrimidines and violate the size complementarity principle of natural nucleobase pairing.

Association of the purine-purine duplexes is remarkable among complexes of deoxyribo- or ribonucleic acids. Mixed sequence purine-purine nucleic acids with a natural backbone and natural nucleobases associating in a duplex structure are unknown.

The present invention provides duplexes with a plurality of purine-purine dyads.

In one aspect, a stable anti-parallel nucleic acid duplex is disclosed comprising a plurality of complementary purine-purine nucleobase dyads. The nucleic acids may further comprise a carbohydrate backbone of ribose or deoxyribose, and phosphate.

In another aspect, a stable anti-parallel nucleic acid duplex is disclosed consisting essentially of a plurality of complementary purine-purine nucleobase dyads. The nucleic acids may further comprise a carbohydrate backbone of ribose or deoxyribose, and phosphate.

Suitable carbohydrate backbones include, for example, D-ribose and 2'-deoxy-D-ribose.

The nucleic acid duplex can form nucleobase dyads comprising purine-purine pairing through complementary Watson-Crick interactions. In some embodiments, the complementary purine-purine nucleobase dyads are contiguous. In a particular embodiment, the nucleic acid duplex comprises a plurality of contiguous purine-purine dyads. In other embodiments, the complementary purine-purine nucleobase dyads are not contiguous.

The nucleic acid duplex can include a nucleobase adopting a tautomer that is a minor species of the nucleobase present in aqueous solution (i.e., an unhybridized nucleobase) in the absence a Watson-Crick interaction.

Nucleic acid duplexes with one or more purine-purine nucleobase dyads may have any one or more of the following pairings:

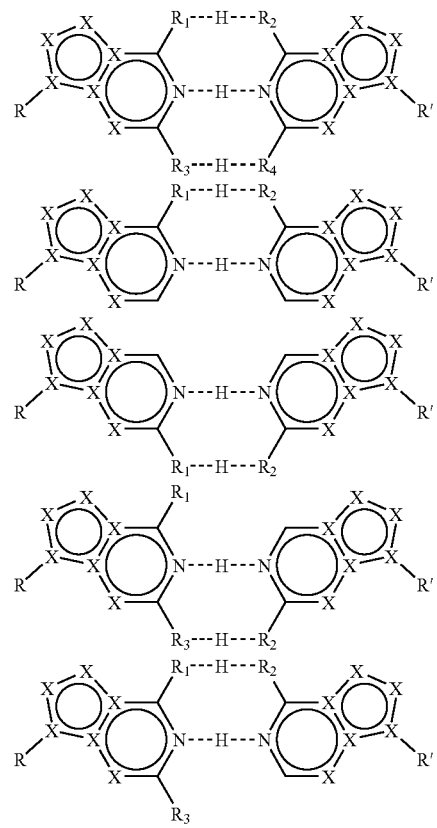

where X is independently selected from the group consisting of C, N, CH, and NH, provided that aromaticity is preserved; each R and R' is selected from the group consisting of ribose and deoxyribose; and each $R_1$, $R_2$, $R_3$, and $R_4$ is selected from the group consisting of hydrogen bond donors —$NH_2$, —SH, and —OH, or the group of hydrogen bond acceptors =O, =S, =NH, —OH, —SH, and —$NH_2$, such that an individual hydrogen atom within a hydrogen bond is associated with one donor and one acceptor.

In another embodiment, the nucleic acid duplexes of the present invention include one or more purine-purine nucleobase dyads having adenosine molecules that are unsubstituted at the N8 position.

Nucleic acid duplexes with one or more purine-purine nucleobase dyads may have the following hydrogen bond donor and acceptor pairings:

| | | |
|---|---|---|
| puADD-puDAA | puAD_-puDAA | puAD_-puDA_ |
| puAAD-puDDA | puAA_-puDDA | puAA_-puDD_ |
| puADA-puDAD | puADA-pu_AD | pu_DA-pu_AD |
| | puADD-pu_AA | pu_DD-pu_AA |
| | puAAD-pu_DA | pu_AD-pu_DA |
| | puADA-puDA_ | puAD_-puDA_ |

In some embodiments, the nucleic acid duplex can comprise nucleobase dyads having the above hydrogen bond donor and acceptor pairings with one or both of the nucleobases of the dyad adopting a tautomer that is a minor species present in aqueous solution in the absence a Watson-Crick interaction.

The nucleic acid duplexes described above may have one or more purine-purine nucleobase dyad consisting of (a) a first purine selected from adenine, 7-deazaadenine, or 3-deazaadenine and (b) a second purine selected from hypoxanthine, 7-deazahypoxanthine, 3-deazahypoxanthine, 7-deazaxanthine, or xanthine.

The nucleic acid duplexes described above may have one or more purine-purine nucleobase dyad consisting of (a) a first purine selected from guanine, 7-deazaguanine, or 3-deazaguanine and (b) a second purine is isoguanine.

In some embodiments, the nucleic acid duplex can comprise a plurality of contiguous purine-purine nucleobase dyads. In one embodiment, the nucleic acid duplex can comprise at least 3 contiguous purine-purine nucleobase dyads. In another embodiment, the nucleic acid duplex can comprise at least 4 contiguous purine-purine nucleobase dyads. In still another embodiment, the nucleic acid duplex can comprise at least 5 contiguous purine-purine nucleobase dyads.

In some embodiments, the nucleic acid duplex can comprise at least one purine-purine nucleobase dyad and a plurality of complementary purine-pyrimidine nucleobase dyads. In another embodiment, the nucleic acid duplex can comprise a plurality of purine-purine nucleobase dyads and a plurality of complementary purine-pyrimidine nucleobase dyads.

In another aspect, a method of hybridizing two nucleic acid molecules includes providing a polynucleotide molecule comprising a region consisting of a plurality of purine nucleotides coupled to a backbone consisting of ribose or deoxyribose, and phosphate, and hybridizing to the polynucleotide molecule an oligonucleotide molecule comprising a plurality of purine nucleotides coupled to a backbone consisting of ribose or deoxyribose, and phosphate, wherein the purine nucleotides of the oligonucleotide molecule are complementary to the plurality of purine nucleotides of the polynucleotide template, thereby forming a stable anti-parallel nucleic acid duplex.

In yet another aspect, a method of hybridizing two nucleic acid molecules includes providing a polynucleotide molecule comprising one or more regions consisting of a plurality of contiguous purine nucleotides coupled to a backbone of ribose or deoxyribose, and phosphate, and hybridizing to the polynucleotide molecule an oligonucleotide molecule comprising one or more regions consisting of a plurality of contiguous purine nucleotides coupled to a backbone consisting of ribose or deoxyribose, and phosphate, wherein the one or more regions of a plurality of contiguous purine nucleotides of the oligonucleotides molecule are complementary to the purine nucleotides of the polynucleotide template, thereby forming a stable anti-parallel nucleic acid duplex having a plurality of contiguous purine-purine dyads.

In yet another aspect, the invention provides a method for detecting the presence or absence of a polymorphism in a polynucleotide molecule, which includes providing a polynucleotide molecule comprising a region having a plurality of contiguous purine nucleotides coupled to a backbone of ribose or deoxyribose, and phosphate, wherein the region of purine nucleotides includes one or more nucleotides characterized by polymorphic variations, and hybridizing to the polynucleotide template an oligonucleotide molecule comprising a plurality of contiguous purine nucleotides coupled to a backbone of ribose or deoxyribose, and phosphate, wherein the plurality of contiguous purine nucleotides of the oligonucleotide molecule are complementary to the plurality of contiguous purine nucleotides of the polynucleotide template having one of the polymorphic variations, thereby forming a stable anti-parallel nucleic acid duplex having a plurality of contiguous purine-purine dyads.

In another aspect, the invention provides a method for detecting the presence or absence of a polymorphism in a polynucleotide molecule, which includes providing a polynucleotide molecule comprising one or more regions having a plurality of contiguous purine nucleotides coupled to a backbone of ribose or deoxyribose, and phosphate, wherein the region of purine nucleotides includes one or more nucleotides characterized by polymorphic variations, and hybridizing to the polynucleotide template an oligonucleotide molecule comprising one or more regions having a plurality of contiguous purine nucleotides coupled to a backbone of ribose or deoxyribose, and phosphate, wherein the plurality of contiguous purine nucleotides of the oligonucleotide molecule are complementary to the plurality of contiguous purine nucleotides of the polynucleotide template having one of the polymorphic variations, thereby forming a stable anti-parallel nucleic acid duplex having a plurality of contiguous purine-purine dyads.

Nucleic acid probes either fully or partially composed of oligopurine regions used to interact with target nucleic acid in purine-purine duplex or chimeric purine-purine/purine-pyrimidine duplex interactions. These probes may be used in assays based on technologies such as quantitative PCR or branched DNA.

Oligonucleotides having purine-purine dyads may also be used in the presence of enzymatic functions that require purine-pyrimidine interaction to proceed. Such enzyme functions include, but are not limited to, polymerase activity, ligase activity, restriction cleavage, and mismatch repair. Purine-purine interaction in this case can serve structural purposes without interfering with enzyme-mediated processes intended to take place at other regions of nucleic acids, either in the molecules involved in the purine-purine interaction or in other simultaneously present nucleic acids.

Oligonucleotides having purine-purine dyads may also be used in the presence of dye molecules that signal the presence of regions of nucleic acid duplex. Such dyes include, but are not limited to, Ethidium Bromide, SYBR Green, and LC Green. Purine-purine interaction in this case will be undetectable by the dye and thus allow the dye to detect purine-pyrimidine target duplexes.

Labeling of Oligonucleotides

Regardless of whether the oligonucleotides of the invention are synthesized from nucleic acids, modified nucleic acids, nucleic acid analogs, or any combination or variation thereof, the molecules that are used to practice this invention can be labeled with a suitable label/reporter moiety. For example, the oligonucleotides of the invention may be labeled with a label or with multiple labels selected from the group of labels consisting of dyes, fluorescent labels, luminescent labels, radioactive labels, antigens, haptens, enzymes, enzyme substrates, protecting groups, and chemically reactive groups. Other labels may also be used, in addition to, or in conjunction with, these labels.

As used herein, the term "label" in reference to nucleobase oligomers refers to any moiety that can be attached to the oligomer and: (i) provides a detectable signal, where the signal can be in the visible wavelength spectrum or any other wavelength or particle type, e.g., a radioisotope decay particle; (ii) interacts with a second label to modify the detectable signal provided by the second label, i.e., energy transfer label pairs, e.g., FRET pairs; (iii) stabilizes hybridization, i.e., duplex formation; (iv) confers a capture function, e.g., hydrophobic affinity, antibody/antigen, ionic complexation, or (v) changes a physical property, such as electrophoretic mobility, hydrophobicity, hydrophilicity, solubility, or chromatographic behavior. Labeling can be accomplished using any one of a large number of known techniques employing known labels, linkages, linking groups, reagents, reaction conditions, and analysis and purification methods. Labels include light-emitting or light-absorbing compounds which generate or quench a detectable fluorescent, chemiluminescent, or bioluminescent signal (Kricka, L. in Nonisotopic DNA Probe Techniques (1992), Academic Press, San Diego, pp. 3-28). As used herein, the terms "label" and "reporter" may in some cases be used interchangeably.

It is contemplated that the nucleobase oligomers of the invention can be labeled with any labeling moiety or technique currently known in the art for labeling nucleic acids, modified nucleic acids or nucleic acid analogs. It is not intended that the invention be limited in any way to any particular labeling method. Techniques for labeling of nucleic acids, modified nucleic acids and nucleic acid analogs are widely known in the art, and thorough discussion and detailed protocols for labeling are available from many sources. For example, see, "Non-Radioactive Labeling, A Practical Introduction," Garman, Academic Press, San Diego, Calif (1997).

Non-limiting examples of reporter/label moieties suitable for the direct labeling of oligonucleotides include, but are not limited to, a quantum dot, a dextran conjugate, a branched nucleic acid detection system, a chromophore, a fluorophore, a quencher, a spin label, a radioisotope, an enzyme, a hapten, an acridinium ester and a chemiluminescent compound. Quenching moieties are also considered labels. Other suitable labeling reagents and preferred methods of label attachment would be recognized by those of ordinary skill in the art. Any examples cited herein are intended to be merely illustrative and are non-limiting.

A label or reporter moiety can be linked to any position within the nucleobase oligomers. A label can reside at a terminus of the oligomer or at a position internal to the oligomer (e.g., within or attached to the nucleobases). The nucleobase can be labeled either following synthesis of the complete oligomer, or incorporated during synthesis of the oligomer.

Non-limiting examples of fluorescent reporter dyes useful for labeling biomolecules (fluorophores) include, but are not limited to, 5(6)-carboxyfluorescein (Flu), 2',4',1,4-tetrachlorofluorescein; and 2',4',5',7',1,4-hexachlorofluoresc-ein, other fluorescein dyes (see, e.g., U.S. Pat. Nos. 5,188,934; 6,008,379; 6,020,481, incorporated herein by reference), 6-((7-amino-4-methylcoumarin-3-acetyl)amino)hexanoic acid (Cou), 5(and 6)-carboxy-X-rhodamine (Rox), other rhodamine dyes (see, e.g., U.S. Pat. Nos. 5,366,860; 5,847, 162; 5,936,087; 6,051,719; 6,191,278; 6,248,884, incorporated herein by reference), benzophenoxazines (see, e.g., U.S. Pat. No. 6,140,500, incorporated herein by reference) Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), other cyanine dyes (Kubista, WO 97/45539), 6-carboxy-4',5'-dichloro-2',7'-dimethoxyfluorescein (JOE), 5(6)-carboxy-tetramethyl rhodamine (Tamara), Dye 1 Dye 2 or the Alexa dye series (Molecular Probes, Eugene, Oreg.).

As used herein in reference to a fluorescent label, "quenching" means a decrease in the fluorescence of a fluorescent label (i.e., a fluorescent reporter moiety). A donor moiety may be a fluorophore, and an acceptor moiety (a "quencher" moiety) may be fluorophore or may be a non-fluorescent moiety. In some embodiments, the decrease in fluorescence is caused by fluorescence resonance energy transfer (FRET) associated with a quencher moiety, regardless of the mechanism. Energy transfer may occur between members of a set of energy transfer labels, the set of energy transfer labels having at least one acceptor moiety and at least one donor moiety. An energy transfer set may contain more than one donor moiety and/or more than one acceptor moiety. Transfer of energy between donor and acceptor moieties may occur through any energy transfer process, such as through the collision of the closely associated moieties of an energy transfer set(s) or through a non-radiative process such as FRET. In embodiments of the invention, a nucleobase oligomer may have at least one energy transfer set of labels. The labels of an energy transfer set may be linked to oligomer termini, or may be linked to sites within a nucleobase oligomer. Alternatively, or in addition, an acceptor moiety and a donor moiety may be coupled to different oligomers. Non-limiting examples of quenching moieties include but are not limited to diazo-containing moieties such as aryldiazo compounds, e.g., 4-((4-(dimethylamino)phenyl)azo) benzoic acid (dabcyl), dabsyl, homologs containing one more additional diazo and/or aryl groups; e.g., Fast Black, (see, e.g., U.S. Pat. No. 6,117,986), cyanine dyes (see, e.g., U.S. Pat. No. 6,080,868), Black Hole Quenchers 1 & 2, Dark Quencher, Deep Dark Quencher 1 & 2, QSY 7, QSY 9, QSY 21, QSY 35, and other chromophores such as anthraquinone, malachite green, nitrothiazole, and nitroimidazole compounds.

Pairs of labels that constitute energy transfer label sets (or energy transfer label pairs) are also useful with the nucleobase oligomers of the invention in energy transfer applications (e.g., fluorescence resonance energy transfer or FRET probes or probes suitable for use in real-time PCR analysis, i.e., TAQMAN analysis). Energy transfer probe sets have found widespread and diverse uses in cellular/molecular biological studies, and protocols for their synthesis and use are widely known in the art. See, for example, WO 99/21881, WO 99/22018 and WO 99/49293.

Energy transfer pairs can be used to detect/monitor nucleobase hybridization between a nucleobase oligomer of the invention and a target or template polynucleotide. When used in this manner, the nucleobase oligomers can be labeled with a suitable energy transfer pair prior to use as a probe. Suitable energy transfer pairs to use in this type of application are known in the art, where such a probe is sometimes termed a "linear beacon" or a "molecular beacon" (see, e.g., WO99/21881).

The formation of a hybridization complex between a suitably labeled nucleobase oligomer and a target polynucleotide sequence can be monitored by measuring at least one physical property of at least one member of the energy transfer set that is detectably different when the hybridization complex is formed as compared with when the nucleobase oligomer exists in a non-hybridized state. This change in detectable signal results from the change in efficiency of energy transfer between donor and acceptor moieties caused by hybridization of the oligomer to the target sequence.

Non-limiting examples of enzymes that can be used as labels include, but are not limited to, alkaline phosphatase (AP), horseradish peroxidase (HRP), soy bean peroxidase (SBP), ribonuclease and protease.

Another class of labels includes hybridization-stabilizing moieties which serve to enhance, stabilize, or influence hybridization of duplexes and cross-linking functional groups (Blackburn and Gait, Eds., "DNA and RNA Structure" in Nucleic Acids in Chemistry and Biology, 2nd Edition, (1996) Oxford University Press, pp. 15-81). Yet another class of labels affects the separation or immobilization of a molecule by specific or non-specific capture, for example biotin, digoxigenin, and other haptens (Andrus, "Chemical methods for 5' non-isotopic labeling of PCR probes and primers" (1995) in PCR 2: A Practical Approach, Oxford University Press, Oxford, pp. 39-54). Suitable haptens include fluorescein, biotin, 2,4-dinitrophenyl, digoxigenin, lipopolysaccharide; apotransferrin; ferrotransferrin; insulin; a cytokine; gp120; β-actin; leukocyte function-associated antigen 1 (LFA-1; CD11a/CD18); Mac-1 (CD11b/CD18); glycophorin; laminin; collagen; fibronectin; vitronectin; an integrin, ankyrin; fibrinogen, Factor X; inter-cellular adhesion molecule 1 (ICAM-1); inter-cellular adhesion molecule 2 (ICAM-2); spectrin, fodrin; CD4; a cytokine receptor; an insulin receptor; a transferrin receptor; Fe+++; polymyxin B; endotoxin-neutralizing protein (ENP); an antibody-specific antigen; avidin; streptavidin; and biotin. Non-radioactive labeling methods, techniques, and reagents are reviewed in: Non-Radioactive Labeling, A Practical Introduction, Garman (1997) Academic Press, San Diego. In some embodiments, the terms "label" and "reporter" are used interchangeably.

Articles of Manufacture

The present invention provides articles of manufacture (e.g., kits) comprising at least one nucleobase oligomer of the invention. In certain embodiments, kits serve to facilitate the performance of a process, method, assay, analysis or manipulation of interest by assembling two or more components used to carry out the methods. Kits can contain any chemical reagent, enzyme, or equipment required for use of the method. In certain embodiments, kits contain components in pre-measured amounts to minimize the need for measurements by end-users. In certain embodiments, kits include instructions for performing one or more methods of the invention. In certain embodiments, the kit components are optimized to operate in conjunction with one another.

When used in kits of the invention, the nucleobase oligomer can be made sequence-specific for a given target sequence, and can be labeled or unlabeled. If the oligomer is labeled, the label chosen will be suitable for use in the intended application. The oligomers of the invention can be packaged in suitable containers, such as tubes or ampules, and can be packaged in a dried (e.g., lyophilized) form, or in an aqueous form. If necessary, the articles of manufacture in the kits can be chilled or frozen during shipping and/or storage. Any article of manufacture comprising oligomers of the invention can further include a description of the product, specifications of the product, or instructions for use of the product.

In addition, kits of the present invention can also include, for example but are not limited to, apparatus and reagents for sample collection and/or purification, apparatus and reagents for product collection and/or purification, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and shipping, for example, in a box having a lid.

The nucleobase oligomers provided in the kits may or may not be labeled. In other embodiments, the invention provides kits comprising nucleobase oligomers as well as means for labeling the oligomers. In other embodiments, the invention provides kits comprising labeled or unlabeled oligomers as well as means (e.g., apparatus and/or reagents) for the visualization or detection the oligomers.

The invention also provides kits to facilitate use of the oligomers of the invention in various methods, e.g., any method that involves sequence-specific hybridization. Materials and reagents to carry out these methods can be provided in kits to facilitate execution of the methods. A kit of the invention comprises at least one nucleobase oligomer of the invention, and optionally can additionally comprise a number of additional components, including but not limited to (i) one or more buffers; (ii) one or more nucleotide triphosphates; (iii) a nucleic acid amplification master mix; (iv) one or more polymerase enzymes, or (v) reagents or equipment suitable for the isolation/purification of a nucleic acid product. In one embodiment, the kit comprises at least two oligonucleotide primers suitable for use as primers in a PCR reaction.

In some embodiments, the present invention provides kits for conducting real-time PCR analysis. These kits can include, for example but are not limited to, reagents for the collection of a sample, a reverse transcriptase, primer suitable for reverse transcriptase initiation and first strand cDNA synthesis, at least one nucleobase oligomer of the invention, primer suitable for second strand cDNA synthesis, a DNA-dependent DNA polymerase, free deoxyribonucleotide triphosphates, and reagents suitable for the isolation/purification of the cDNA molecules produced by the reaction.

In one embodiment providing kits of the invention, a single nucleobase oligomer is provided that is specific for a single target sequence. In other embodiments, multiple nucleobase oligomers specific for a plurality of targets are provided in the kit. In some embodiments, kits are provided having the nucleobase oligomers of the invention affixed to a solid phase or surface. In certain embodiments, the kits of the invention may be used to sequence at least one target nucleic acid template.

In still other embodiments, the present invention provides kits for the analysis of gene expression using the oligomers of the invention. These kits can include multiple nucleobase oligomers of the invention affixed to a suitable array or chip configuration, as well as reagents required for the detection/visualization of hybridized complexes.

In still another aspect, the invention provides kits comprising an oligonucleotide molecule comprising a plurality of purine nucleotides coupled to a backbone consisting of ribose or deoxyribose, and phosphate, wherein the purine nucleotides of the oligonucleotide molecule are complementary to a plurality of purine nucleotides of a polynucleotide template. In another aspect, the invention provides kits comprising an oligonucleotide primer comprising a plurality of purine nucleotides coupled to a backbone consisting of ribose or deoxyribose, and phosphate, wherein the purine nucleotides of the oligonucleotide molecule are complementary to a plurality of purine nucleotides of a polynucleotide template. Kits comprising oligonucleotide primers may further include other reagents necessary for primer-initiated synthesis, including dNTPs and suitable buffer components.

In another aspect, the invention provides kits comprising an oligonucleotide molecule comprising one or more regions having a plurality of contiguous purine nucleotides coupled to a backbone of ribose or deoxyribose, and phosphate, wherein the purine nucleotides of the oligonucleotide molecule are complementary to a polynucleotide template comprising one or more regions having a plurality of contiguous purine nucleotides coupled to a backbone of ribose or deoxyribose, and phosphate.

Such kits may be useful in diagnostic and research settings.

Nucleobase oligomer duplexes of the invention will be useful to form structural elements of kits, such as the short duplexes used to immobilize target nucleic acids to a surface as in Versant® bDNA kits. Nucleobase oligomer duplexes of the invention allows other regions of a target oligonucleotide to be involved in the many signaling or amplification processes dependent on the formation of canonical Watson-Crick duplexes without interference from the structural element.

Nucleobase oligomers of the invention will find utility in situations where canonical Watson-Crick duplexes may be affected by common processes of molecular biology. Duplexes of purine-purine nucleic acids will not act as substrates in many enzymatically-mediated processes, such as polymerase replication and amplification, ligation, restriction, and mismatch repair, which depend on recognition of a duplex nucleic acid.

In one embodiment, polymerase-dependent amplification reactions proceed without the nucleobase oligomer duplex structure of the invention acting as a site of polymerization initiation. For example, oligonucleotides with sequences complementary to oligonucleotides immobilized on a surface could be used to form nucleobase oligomer duplex structures of the invention, which will be inert in the presence of these enzymatically-mediated processes.

In another embodiment, small molecules that target duplex nucleic acids will exhibit altered interaction with nucleobase oligomer duplex structures of the invention. This allows, for example, dyes such as SYBR Green I to be used to specifically detect formation of a canonical duplex in the presence of a nucleobase oligomer duplex of the invention, because the nucleobase oligomer duplex remains undetectable in monitoring fluorescence of the dye.

Applications and Methods of Use

The compositions and methods of the present invention find use in a variety of applications. Indeed, the nucleobase oligomers of the present invention find use in applications where nucleobase oligomers are used in a hybridization protocol. For example, the compositions and methods of the invention find use in the analysis of gene expression. It is not intended that the invention find use in only the few applications discussed herein, as one familiar with the art will immediately recognize a variety of uses for the oligomers of the invention. The uses cited herein are intended to be exemplary and not limiting, and such examples are not exhaustive. It is understood that use of the invention is not limited to any particular application cited herein, as the invention finds use with any protocol that incorporates oligomeric nucleobase sequences as probes or primers.

When used as probes it is a requirement that the nucleobase oligomers hybridize to a target sequence with sequence specificity. Thus, when used as a probe, there are no additional limitations on specific features of the nucleobase oligomer.

Real-Time Monitoring of PCR Products

The general application of energy transfer (e.g., FRET) labels in conjunction with the nucleobase oligomers of the invention are discussed above. Another application of energy transfer labeling is the synthesis of probes suitable for real-time monitoring of the accumulation of PCR products, i.e., TAQMAN® analysis.

The oligomers of the invention find use FRET-type probes in real-time quantitative PCR analysis. Real-time PCR analysis refers to the monitoring of accumulating PCR products (also known as a fluorogenic 5' nuclease assay, i.e., TAQMAN analysis. Methods for the synthesis and use of TAQMAN probes are well known in the art. See, for example, Holland et al., Proc. Natl. Acad. Sci. USA 88:7276-7280 [1991] and Heid et al., Genome Research 6:986-994 [1996]).

In general, the TAQMAN PCR procedure uses two oligonucleotide primers to generate an amplicon from a template typical of a PCR reaction. A third non-priming nucleobase oligomer (not necessarily a nucleotide oligomer) is also included in the reaction (the TAQMAN probe). This probe has a structure that is non-extendible by Taq DNA polymerase enzyme, and is designed to hybridize to nucleotide sequence located between the two PCR primers. The TAQMAN probe is labeled with a reporter fluorescent dye and a quencher fluorescent dye on opposite termini. The oligomers of the invention find use as a TAQMAN probe. The laser-induced emission from the reporter dye is quenched by the quenching dye when the two dyes are located close together, as they are when the probe is annealed to the PCR amplicon.

TAQMAN assay data are expressed as the threshold cycle (CT), which is the minimum number of PCR cycles required to achieve a statistically significant detectable level of fluorescence from the reporter dye. Fluorescence values are recorded during every PCR cycle and represent the amount of product amplified to that point in the amplification reaction.

Analysis of Gene Expression

Gene expression may be analyzed by detection of target gene or other nucleobase sequences in a sample indicative of gene expression, such as a cDNA derived from mRNA obtained from a cell of interest. For example, a cDNA library derived from a cell of interest may be contacted with a plurality of probes comprising the nucleobase oligomers of the present invention in order to detect the presence of nucleobase sequences complementary to those of the nucleobase oligomers. Such analysis may be used to determine the expression of particular nucleobase sequences and so be indicative of the expression of genes including such nucleobase sequences.

Such gene expression analysis may be performed on similar cells under different conditions or from cells during different parts of the cell cycle (see, for example, DeRisi et al., Science 278:680-686 (1997)). Comparison of the results of such gene expression analysis may be used to determine what gene activity is altered under the different conditions or during the different parts of the cell cycle. Similarly, comparison between normal cells and cancerous cells may indicate differences in gene expression between the normal and the cancerous conditions. Thus, for example, where cDNAs are obtained from normal and cancerous cells, comparison of the hybridization between such cDNAs and with nucleobase oligomers having features of the invention may be used to determine differences in gene expression between normal and cancerous cells.

The nucleobase oligomers provided by the present invention find use in hybridization assays, e.g., in the analysis of gene expression. The nucleobase oligomers of the invention are used as probes in two general capacities. First the oligomers of the invention can be labeled and used to detect a target polynucleotide. Second, the oligomers of the invention can be immobilized to a solid phase and used in an array or chip type gene expression analysis system. It is not intended that the oligomers of the present invention be limited to use in any particular hybridization format, protocol or conditions, as one familiar with the art is familiar with a variety of hybridization protocols, and recognizes well the advantages of the present invention as they apply to many hybridization formats.

In the first aspect, the oligomer of the invention is labeled prior to hybridization and use as a probe. It is not intended that the present invention place any restriction on how the labeled probe is used. As used herein, the term "label" refers to any moiety that allows isolation, cloning, detection, visualization, or quantitation of a target nucleotide sequence. The label that is covalently attached to an oligomer may be detectable by itself (e.g., fluorescein or a radioisotope), or conversely, may not be directly visualized until interaction with a secondary reagent (e.g., a biotin/strepavidin coupled dye, or a conjugated enzyme that requires the presence of a chromogenic substrate). The labeled oligomer when in a complex (e.g., a duplex) with a target sequence can be detected using a suitable method, for example but not limited to radiometric detection, colorimetric determinations, fluorescence, chemiluminescence, bioluminescence and enzyme-coupled assays. Numerous oligomer labeling/detection techniques are widely known in the art, all of which find use with the present invention. It is not intended that the present invention be limited to any particular labeling method.

In the second aspect, the hybridization reactions take place in high throughput formats, as known in the art. Generally, the high throughput hybridization formats use a probe (i.e., an oligomer of the invention) that is affixed to a solid support. The solid support can be any composition and configuration, and includes organic and inorganic supports, and can comprise beads, spheres, particles, granules, planar or non-planar surfaces, and/or in the form of wells, dishes, plates, slides, wafers or any other kind of support. In some embodiments, the structure and configuration of the solid support is designed to facilitate robotic automation technology. The steps of detecting, measuring and/or quantitating can also be done using automation technology.

In some embodiments, the hybridization format is an "array", "microarray", "chip" or "biochip" as widely known in the art (see, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000]). In general, array formats facilitate automated analysis of large numbers of samples and/or have a large number of addressable locations, so that patterns of gene expression for a very large number of genes can be studied very rapidly. The oligomers of the invention, when used as probes, find use with array formats, and it is not intended that the oligomer probes of the present invention be limited to use in any particular array or hybridization format.

The use of polynucleotide samples in hybridization assays typically necessitate the labeling of the polynucleotide pool prior to hybridization, so that an interaction between the immobilized probe and the target can be detected. A variety of polynucleotide labeling techniques are known in the art, and it is not intended that the present invention be limited to any particular polynucleotide labeling method. The labeled polynucleotide sample permits the detection of those species that are in a duplex with a probe affixed to a solid support, such as in a microarray. A labeled polynucleotide in a duplex with the affixed probe can be detected using a suitable detection method.

In one embodiment of the invention, the labeling of the polynucleotide pool (comprising either RNA or DNA molecules) is accomplished by incorporating a suitable label into the nascent polynucleotide molecules at the time of synthesis. For example, dye-coupled GTP can be incorporated into a nascent RNA chain. In an alternative embodiment, the labeling of the polynucleotide pool is accomplished after the polynucleotide pool is synthesized. In these embodiments, the RNA or DNA molecules are labeled using a suitable label that is coupled (i.e., conjugated or otherwise covalently attached) to the polynucleotides after chain synthesis.

In still other embodiments, an unlabeled pool of polynucleotides in a sample can be used directly in hybridization or gene expression analysis using methods that do not required a labeling step. For example, duplex formation with an affixed probe can be detected using surface plasmon resonance (SPR) (See, e.g., SPREETA™ SPR biosensor (Texas Instruments, Dallas, Tex.), and BIACORE 2000 (BIACORE®, Uppsala, Sweden). Resonant light scattering methods can also be used to detect duplex formation in a hybridization analysis using probes that have not been otherwise labeled (Lu et al., Sensors 1:148-160 [2001]).

It is not intended that the present invention be limited to any particular labeling, probing, or hybridization method. One skilled in the art is familiar with a wide variety of such protocols and reagents, all of which find use with the oligomers of present invention.

Use in Hybridization Reactions

The nucleobase oligomers of the invention find use in any method involving hybridization, i.e., the forming of a complex between two complementary nucleobase sequences. The complementarity need not be 100%, as effective hybridizations can occur when there is less than 100% complementarity.

The potential uses of the nucleobase oligomers of the invention are not in any way limited. Thus, one familiar with the art recognizes that the specific conditions to be used in hybridization reactions as practiced using compositions of the invention are similarly unlimited, and are dependent on the particular application and the primary sequence of the oligomers used. A wide variety of sources are available that describe hybridization conditions for particular application; see, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000].

Immobilization on a Solid Support (e.g., Arrays)

In one aspect, the invention pertains to compositions and methods for making and using nucleobase oligomers that are affixed to a solid support. A wide variety of solid supports find use with the invention, and it is not intended that the invention be limited to the use of any particular type of solid support. Similarly, it is not intended that the manner in which the nucleobase oligomers are affixed to the solid support be limited in any way.

In one embodiment, the support-bound nucleobase oligomers form an array (e.g., a chip) of oligomers. Detailed methods for making and using arrays comprising polymeric nucleobase structures (e.g., nucleic acid, modified nucleic acids, nucleic acid analogs, or chimeric structures) are well-known in the art and are described in many sources. See, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000]. Any methods for the synthesis and use of nucleic acids, modified nucleic acids and nucleic acid analogs with solid supports, and more specifically arrays, are applicable for use with the present invention.

Because the location and sequence of each support bound oligomer is known, arrays can be used to simultaneously detect, identify and/or quantitate the presence or amount of one or more target sequences in a sample. For example, a target sequence can be captured by the complementary nucleobase oligomer on the array surface and then the complex containing the target sequence can be detected. Since the sequence of the nucleobase oligomer is known at each location on the surface of the array, the sequence of target sequence(s) can be directly detected, identified and/or quantitated by determining the location of a detectable signal generated on the array. Thus, arrays are useful in diagnostic applications or in screening compounds, e.g., during development of therapeutic compounds.

In one embodiment, the oligomers can be synthesized on the surface in a manner suitable for deprotection but not cleavage from the synthesis support (see, e.g., Weiler et al., "Hybridization based DNA screening on peptide nucleic acid (PNA) oligomer arrays," Nucl. Acids Res., 25(14):2792-2799 (1997)). In still another embodiment, one or more nucleobase oligomers can be covalently linked to a surface by the reaction of a suitable functional group on the oligomer with a functional group of the surface (see, e.g., Geiger et al., PNA Array technology in molecular diagnostics, Nucleosides & Nucleotides 17(9-11):1717-1724 (1998)). This method is advantageous since the oligomers immobilized on the surface can be highly purified and attached using a defined chemistry, thereby possibly minimizing or eliminating non-specific interactions.

Methods for the chemical attachment of nucleobase oligomers to solid support surfaces can involve the reaction of a nucleophilic group, (e.g., an amine or thiol) of the oligomer to be immobilized, with an electrophilic group on the solid support surface. Alternatively, the nucleophile can be present on the support and the electrophile (e.g., activated carboxylic acid) can be present on the oligomer.

Conditions suitable for the immobilization of a nucleobase oligomer to a surface are widely known in the art. The immobilization reaction to a solid support is analogous to a labeling reaction, where the label is substituted with the surface to which the polymer is to be linked. It is not intended that the invention be limited to any particular immobilization chemistry or method.

Numerous types of solid supports derivatized with amino groups, carboxylic acid groups, isocyantes, isothiocyanates and malimide groups are commercially available. Non-limiting examples of suitable solid supports include chips of any type (e.g., arrays), membranes, glass, controlled pore glass, polystyrene particles (beads), silica and gold nanoparticles. All of the above recited methods of immobilization are not intended to be limiting in any way but are merely provided by way of illustration.

Detection/Identification of Biological Organisms

The nucleobase oligomers of the invention find use in the detection, identification and/or enumeration of biological organisms, and especially, pathogens. Such organisms can include viruses, bacteria and eucarya in food, beverages, water, pharmaceutical products, personal care products, dairy products or in samples of plant, animal, human or environmental origin. The nucleobase oligomers find use in the analysis of raw materials, equipment, products or processes used to manufacture or store food, beverages, water, pharmaceutical products, personal care products dairy products or environmental samples. Additionally, the nucleobase oligomers find use in the detection of pathogens (e.g., various bacteria, viruses and eucarya) in clinical specimens, equipment, fixtures or products used to treat humans or animals as well as in clinical samples and clinical environments. For example, the analysis for microorganisms of interest can be performed using FISH or multiplex FISH using probes generated by the invention described herein (See: BP U.S. application Ser. Nos. 09/335,629 and 09/368,089).

The compositions, methods, kits, libraries and arrays of this invention are particularly useful in areas such as expression analysis, single nucleotide polymorphism (SNP) analysis, genetic analysis of humans, animals, fungi, yeast, viruses, and plants (including genetically modified organisms), therapy monitoring, pharmacogenomics, pharmacogenetics, epigenomics, and high throughput screening operations.

Multiplex Analysis

In certain embodiments, the invention provides nucleobase oligomers for use in multiplex hybridization assays. In a multiplex assay, numerous conditions of interest are simultaneously or sequentially examined. Multiplex analysis relies on the ability to sort sample components or the data associated therewith, during or after the assay is completed. In performing a multiplex assay, one or more distinct independently detectable moieties can be used to label two or more different nucleobase oligomers that are to be used simultaneously in an assay. As used herein, "independently detectable" means that it is possible to determine one label independently of, and in the presence of, at least one other additional label. The ability to differentiate between and/or quantitate each of the independently detectable moieties provides the means to multiplex a hybridization assay because the data correlates with the hybridization of each distinct, independently labeled nucleobase oligomer to a particular target sequence sought to be detected in the sample. Consequently, the multiplex assays of this invention can, for example, be used to simultaneously or sequentially detect the presence, absence, number, position or identity of two or more target sequences in the same sample in the same assay.

Genomic Analysis

Nucleobase oligomers may also be used in genomic analysis. For example, a target sample of genomic material may be contacted with a probe comprising a nucleobase oligomer in order to determine whether hybridization occurs. Hybridization between the probe and the target indicates the presence in the target of nucleobase sequence complementary to that of the probe.

In preferred embodiments of the invention, a target sample of genomic material may be contacted with a plurality of probes comprising nucleobase oligomers. Hybridization between one or more of the probes and the target indicates the presence in the target of nucleobase sequence complementary to that of the hybridizing probe sequence(s). Such hybridization may be detected by detecting fluorescence from fluorescent labels attached to the probes; by quenching of fluorescence from fluorescent labels attached to the probes; by antibody binding to antigens on the probes; by detection of radioactivity emitted by radioactive labeled probes; or by other labeling and detection methods.

EXAMPLES

Oligodeoxynucleotides 1-12, shown in Table 1, were prepared as described below to examine association of duplexes through purine-purine interaction. The following nonstandard abbreviations are use to denote nucleobases: isoguanine (J), 5-methylisocytosine (F), hypoxanthine (H), 7-deazaadenine (Z), and 7-deazaxanthine (X). The fluorescent dye and quencher pair 6-fluorescein (FAM) and Black Hole Quencher 1 (BHQ-1) were used on some of the oligodeoxynucleotides for fluorescent monitoring. All oligodeoxyribonucleotide association experiments were conducted in 0.045 M sodium citrate, 0.45 M sodium chloride, pH 7.9 solutions, unless otherwise indicated. Data from denaturation experiments were fitted in S-Plus (Insightful) using cubic smoothing splines. $T_m$s were determined as the maximum of the first derivative of the fitted curve.

TABLE 1

Oligodeoxynucleotides.

```
1   5'-FAM-JGG AGA AAG HJG HG-BHQ-3'   (SEQ ID NO: 5)

2   3'-GJJ HJH HHJ AGJ AJ-5'           (SEQ ID NO: 6)

3   3'-GAA GAG GGA AGA AA-5'           (SEQ ID NO: 7)

4   5'-JGG AGA AAG HJG HG-3'           (SEQ ID NO: 8)

5   5'-FAM-JGG ZGZ AZG HJG HG-BHQ-3'   (SEQ ID NO: 9)

6   5'-FAM-JGH AHA AAH HJG HG-BHQ-3'   (SEQ ID NO: 10)

7ᵃ  3'-T FCC TCT TTC CFC CC-5'         (SEQ ID NO: 11)

8   5'-FAM-CGG AGA AAG TCG TG-BHQ-3'   (SEQ ID NO: 12)

9   3'-GCC TCT TTC AGC AC-5'           (SEQ ID NO: 13)

10ᵃ 3'-T FCC TCT TTJ AGJ AJ-5'         (SEQ ID NO: 14)

11  5'-CGG AGA AAG TCG TG-3'           (SEQ ID NO: 15)

12  3'-GJJ XJX XXJ AGJ AJ-5'           (SEQ ID NO: 16)
```

ᵃA 3' dangling T was added to allow use of a standard solid phase in synthesis.

Oligodeoxyribonucleotide Preparation. Oligodeoxyribonucleotides containing inosine, 7-deazaadenosine, 7-deazaxanthosine, 5-methylisocytidine or isoguanosine were prepared from phosphoramidites (Glen Research) as recommended by the manufacturer. 3'-BHQ-1 solid support (Biosearch Technologies) was used to introduce quenchers. Oligodeoxyribonucleotides were purified by denaturing HPLC with a Wave System (Transgenomic). Oligodeoxyribonucleotide identity was verified by MALDI-TOF on a Voyager-DE mass spectrometer (Applied Biosystems). Observed masses were within 0.2% of the expected value (BHQ-1 easily fragmented losing a mass of 297). Purity was ≧92% for all oligodeoxyribonucleotides, evaluated with capillary electrophoresis using a capillary at 40° C. filled with polyacrylamide and 7M urea on a $^{3D}$CE instrument (Agilent). Oligodeoxyribonucleotides without inosine, 7-deazaadenosine, 7-deazaxanthosine, 5-methylisocytidine, isoguanosine, or dye labels were purchased with anion exchange HPLC purification from Operon Biotechnologies. Oligodeoxyribonucleotide 8 was purchased from Biosearch Technologies purified by anion exchange and then reversed phase HPLC. Extinction coefficients used to determine oligodeoxyribonucleotide concentrations at pH 7.0 were estimated as 90% of the sum of extinction coefficients at 260 nm for the component deoxynucleosides and dyes ($M^{-1}cm^{-1}$): 15400 (A), 11700 (G), 7300 (C), 8800 (T), 6300 (F), 4600 (J), 7700 (H), 9400 (Z), 8440 (X), 21000 (FAM), and 8000 (BHQ-1). Absorbance at 260 nm of $N_1$—H and $N_3$—H tautomers of J fortuitously appears to be nearly equivalent.

Fluorescence measurements. Experiments detecting fluorescence were performed using either MX4000 or MX3000P instruments (Stratagene) with FAM filter sets. Cooling or heating ramps of samples in 96 well microplates were 0.5° C. per 30 s over 10 to 90° C. (MX4000) or 25 to 90° C. (MX3000P), with 75 μL sample volumes and four data points collected at each 0.5° C. increment. Samples were measured in duplicate over one complete cooling and heating cycle. In stoichiometry experiments, oligodeoxyribonucleotide 1 at 125 nM was mixed with 0, 0.2, 0.4, 0.6, 0.8, 1.0, 1.25, 1.5, or 1.75 equivalents of 2. Fluorescence of duplicate samples at each level was measured after a cooling ramp and then holding for 3 min at 25° C. SYBR® Green I dye 10,000× stock solution (Molecular Probes) was diluted 1:99 with 0.045 M sodium citrate, 0.45 M sodium chloride, pH 7.9. SYBR® Green experiments were performed in 75 μL volumes containing 1 μL of the diluted SYBR® Green solution with oligodeoxyribonucleotides at 0.25 μM.

Absorbance measurements. Experiments detecting absorbance were performed using an 8453 spectrophotometer (Agilent) equipped with a Peltier thermostatted cell holder and an 89090A temperature controller. Thermal denaturation experiments were performed with 0.65 mL samples in black wall micro cells with data collection at 1 nm intervals, 0.5 s integration time and utilizing volume correction for temperature changes. Cooling or heating ramps were 1° C. per min over 20 to 80° C. (for duplex 4•2) or 20 to 85° C. (for duplex 11•9). Samples were measured over one or two complete cooling and heating cycles. Mixing curve samples of various mole fractions of 4 and 2 were heated to 75° C. for 3 min and then allowed to stand at room temperature for 24 h. Mixing curve data were collected with the cell holder at 20° C.

CD measurements. Samples contained 4 μM each oligodeoxyribonucleotide strand in 0.65 mL in black wall micro cells. CD spectra were measured at 20° C. and 75° C. with an Aviv 62DS CD Spectrometer at 1 nm intervals and 5 s averaging time.

Gel analysis. Samples of 1 (18 pmol), 1•2 (18 pmol), 8 (9 pmol), and 8•9 (9 pmol) were made by adding the appropriate oligodeoxyribonucleotides to 1 μL of 0.45 M sodium citrate, pH 7.9 and diluting to 20 μL with water. The samples were heated at 75° C. for 3 min, allowed to stand at room temperature for 90 min, and then kept at 4° C. for 30 min. A 4% agarose E-gel (Invitrogen) was stored at 4° C. for 30 min before electrophoresis. The top and bottom surfaces of the gel cassette were kept in contact with small ice-filled plastic bags and a current of 40 mA was applied for 2 min. Samples were loaded onto the gel and a current of 20 mA was applied for 1 h, keeping the gel cassette in contact with ice-filled plastic bags. The gel was imaged with a Gel Doc (Bio-Rad) using Quantity One software.

Figure 2:
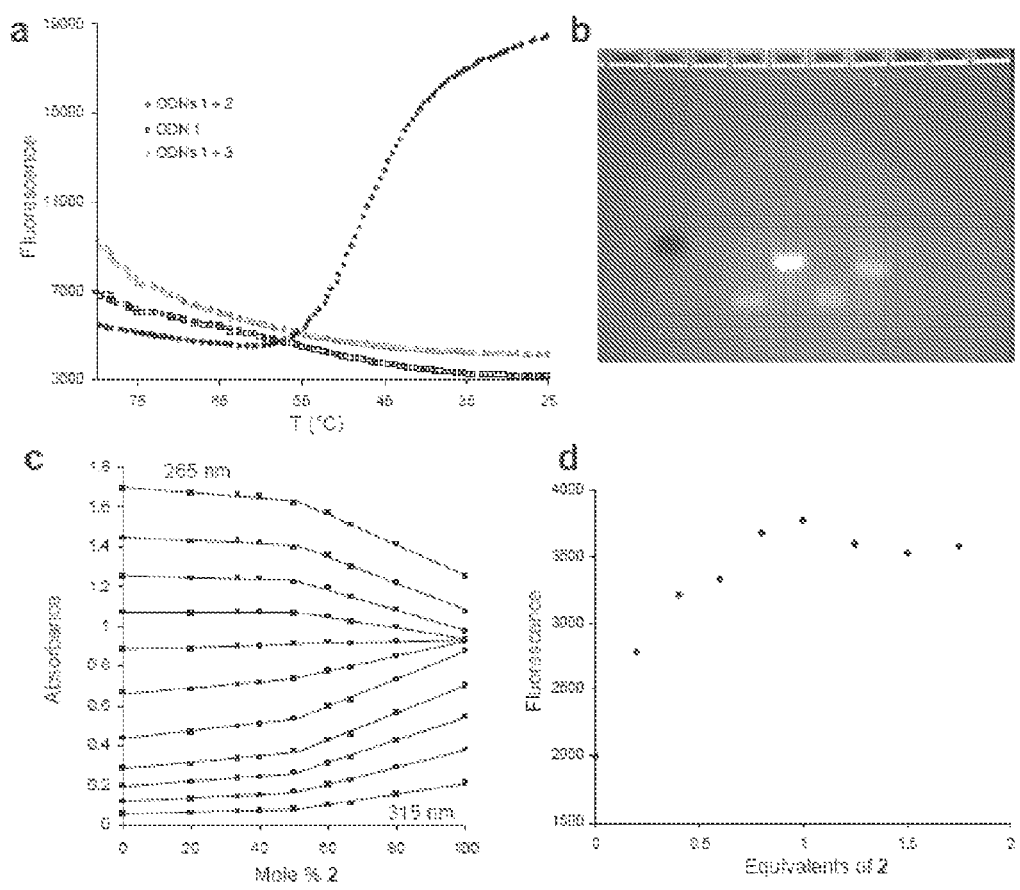
FIG. 2a is a graph showing fluorescence measurements at various temperatures for purine-purine oligonucleotides 1, 2, and 3 each at 1 µM. The graph demonstrates a cooperative temperature-dependent association by monitoring the change in fluorescence of oligonucleotide 1.
FIG. 2b is an electrophoresis gel image showing four lanes with visible fluorescent bands containing oligonucleotides, from left to right 8; 8 and 9; 1; 1 and 2.
FIG. 2c is a plot of absorbance at various molar concentrations (mixing curves) for oligonucleotides 4 and 2 with absorbance from 265 to 315 nm (5 nm intervals shown). The plot shows a discontinuity when equimolar amounts of oligonucleotides 4 and 2 are present demonstrating a 1:1 complex of the oligonucleotides.
FIG. 2d is a plot of measured fluorescence of oligonucleotide 1 when mixed with various amounts of oligonucleotide 2. The plot shows that fluorescence increased until 1 equivalent of oligonucleotide 2 was added. Fluorescence leveled off as the amount of oligonucleotide 2 exceeded 1 equivalent, consistent with a 1:1 complex between oligonucleotides 1 and 2.

Specific pairing of purine-purine duplexes was demonstrated with a series of oligodeoxyribonucleotides (ODNs) shown in Table 1. Oligodeoxyribonucleotides 1 and 2 were designed to form antiparallel duplex 1-2, arraying adenine (A) opposite hypoxanthine (H), and guanine (G) opposite isoguanine (J) as depicted in FIG. 1. Association of strands 1 and 2 was monitored by emission of excited 6-fluorescein (FAM) on 1 with changing temperature. Transitions between single strands and dual strand complex were followed because quenching of excited 5'-FAM by the 3'-quencher (BHQ) is greater when 1 is single-stranded. Oligodeoxyribonucleotide 3 was not expected to form a stable duplex with 1 because the sequences cannot be aligned without a high proportion of mismatched dyads. As shown by the data in FIG. 2, oligodeoxyribonucleotides 1 and 2 demonstrated a clear temperature-dependent cooperative association to duplex 1-2, while no interaction was observed between 1 and 3. FIG. 2 is a plot of fluorescence versus temperature of all-purine oligonucleotide 1, duplex 1-2 with each oligodeoxynucleotide at 1 µM, and a mixture of oligodeoxyribonucleotides 1 and 3 each at 8 µM. The data in the plot demonstrate a cooperative temperature-dependent association of duplex 1-2 detected by monitoring the change in fluorescence of oligodeoxyribonucleotide 1. In contrast to the plot of duplex 1-2, the mixture of oligodeoxyribonucleotides 1 and 3 each at 8 uM, did not provide evidence that a duplex with a significantly higher melting point formed.

Other observations confirmed that oligodeoxyribonucleotides 1 and 2 associated in a 1:1 complex. Nondenaturing gel electrophoresis of a mixture of 1 and 2 yielded a single band migrating as expected for duplex formation. FIG. 2b is a picture showing four lanes with visible fluorescent bands containing, from left to right oligodeoxyribonucleotide 8; oligodeoxyribonucleotides 8 and 9; oligodeoxyribonucleotide 1; oligodeoxyribonucleotides 1 and 2. The shift in mobility of oligodeoxyribonucleotide 1 when mixed with oligodeoxyribonucleotide 2 resembles the shift in mobility of oligodeoxyribonucleotide 8 when mixed with oligodeoxyribonucleotide 9 to form canonical duplex 8-9.

In addition, mixing curves of oligodeoxyribonucleotides 4 (oligodeoxyribonucleotide 1 lacking fluorophore and quencher) and 2 indicated a 1:1 complex. FIG. 2c is a plot of mixing curves for oligodeoxyribonucleotides 4 and 2 of absorbance from 265 to 315 nm (5 nm intervals shown). The plot shows a discontinuity when equimolar amounts of oligodeoxyribonucleotides 4 and 2 are present, thus, demonstrating a 1:1 complex of the oligodeoxyribonucleotides.

Mixing curves of oligodeoxyribonucleotides 1 and 2 also indicated a 1:1 complex by monitoring fluorescence of 0 to 1.75 equivalents of oligodeoxyribonucleotide 2 when mixed with oligodeoxyribonucleotide 1. FIG. 2d is a plot of measured fluorescence of oligodeoxyribonucleotide 1 when mixed with various amounts of oligodeoxyribonucleotide 2. Fluorescence increased until 1 equivalent of oligodeoxyribonucleotide 2 was added. Fluorescence leveled off as the amount of oligodeoxyribonucleotide 2 exceeded 1 equivalent, consistent with a 1:1 complex between oligodeoxyribonucleotides 1 and 2.

In addition, when all Na$^+$ in solution was replaced with Li$^+$, there was a negligible effect on the association of duplex 1-2, indicating association was not a result of well-known G or J multiplexes.

Figure 3:
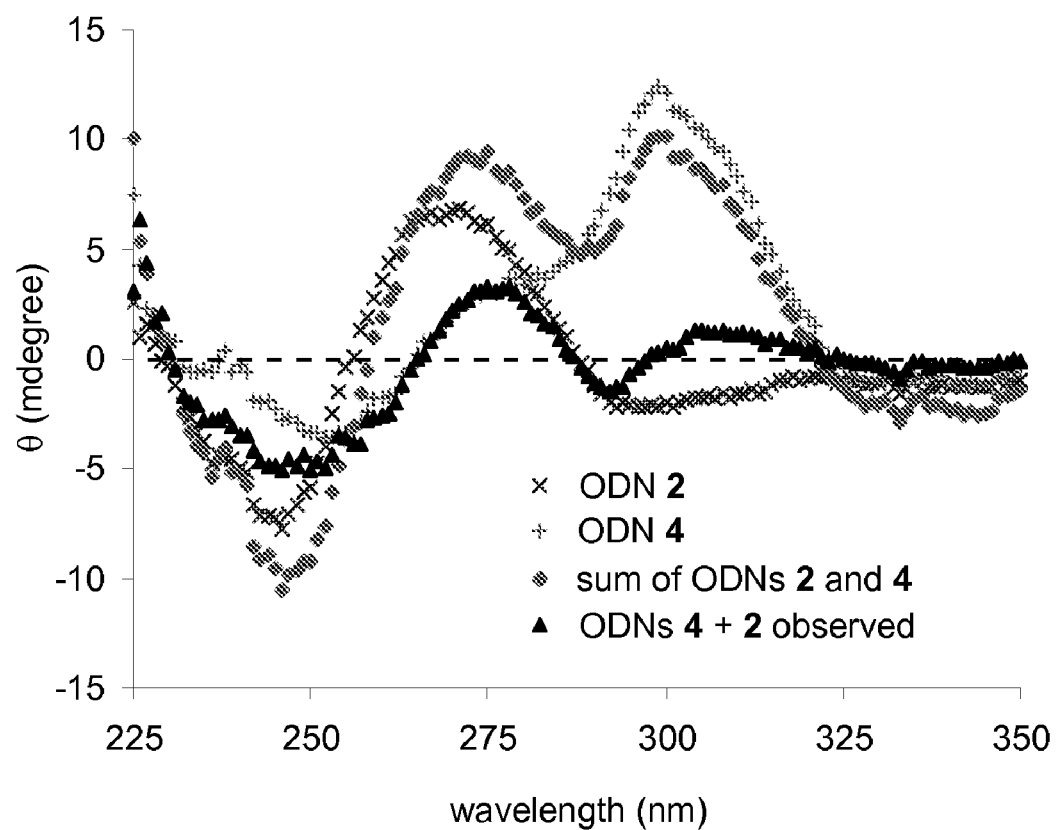
FIG. 3 shows a circular dichrosim (CD) spectroscopy plot of purine-purine duplex 4-2 and oligonucleotides 4 and 2. The plots show that duplex 4-2 has a different CD spectrum than the individual oligonucleotides.

CD spectroscopy also indicated interaction between oligodeoxyribonucleotides 4 and 2. FIG. 3 is a circular dichrosim (CD) spectroscopy plot of purine-purine duplex 4-2. A mixture of oligodeoxyribonucleotides 4 and 2 (each strand at 4 µM) at 20° C. produced a CD scan with positive bands near 275 and 300 nm and a negative band near 245 nm. The sum of the individual scans (at 4 µM and 20° C.) of oligodeoxyribonucleotides 4 and 2 demonstrate changes in the CD scan with formation of duplex 4-2.

Interaction of additional poly-purine sequences supported Watson-Crick interaction in purine-purine association. Although duplex 1-2 appears likely to arise from anti-anti Watson-Crick interaction of the constituent purines, syn-anti Hoogsteen interaction is possible for A•H and G•J pairs.

Figure 4:
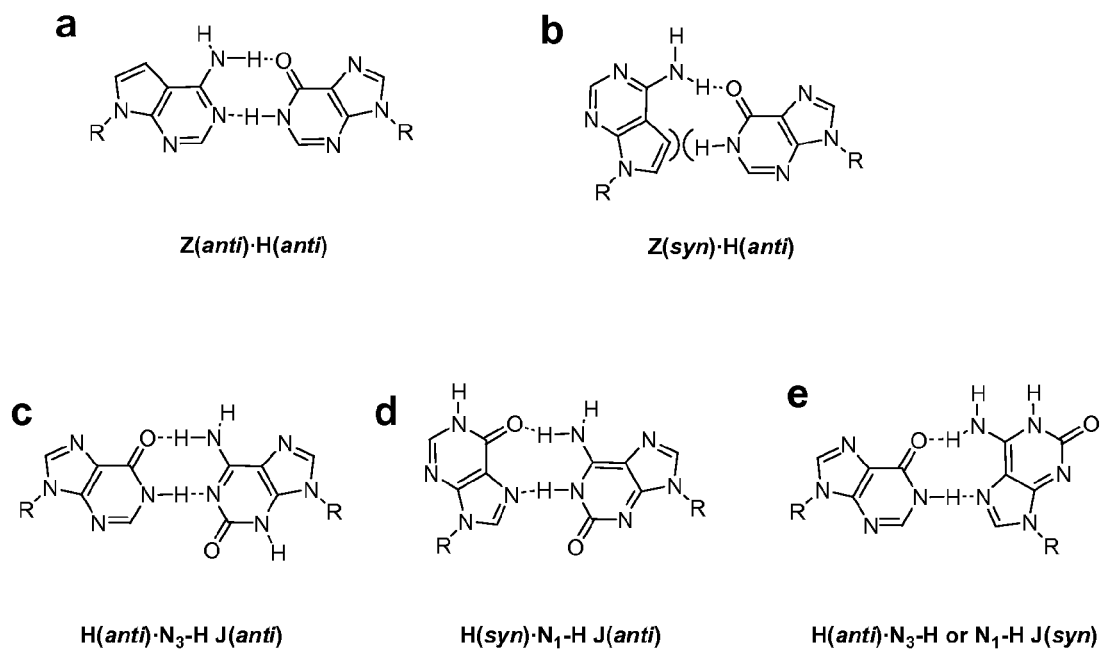
FIG. 4 depicts various duplex pairing conformations including Z(anti) H(anti) conformation (a), Z(syn)-H(anti) conformation (b), H(anti) N3-H J(anti) conformation (c), H(syn) N1-H J(anti) conformation (d), and H(anti) N3-H or N1-H J(syn) conformation (e).

FIG. 4 shows various duplex pairing conformations of H•Z and H•J pairing, which support the duplex associations described herein. In oligonucleotide 5, three adenines of oligodeoxyribonucleotide 1 were changed to 7-deazaadenine (Z). If WA pairs in duplex 1-2 are in anti-anti conformation, substitution with anti-anti H•Z pairs should negligibly affect duplex formation in 5-2 (4a). In contrast, if H•A pairs in duplex 1-2 are in syn-anti conformation, corresponding syn-anti H•Z pairs in duplex 5•2 would be disrupted and the duplex should be destabilized relative to 1-2 (4b). In oligodeoxyribonucleotide 6, three guanines of oligodeoxyribonucleotide 1 were changed to H. If G•J pairs in duplex 1-2 are in anti-anti conformations, the introduction of three H•J pairs in duplex 6-2 could result in a less stable duplex with the oxygen atom on J lacking an opposing donor to form a third hydrogen bond (4c). If, however, G•J pairs in duplex 1-2 are in syn-anti conformations, the corresponding H•J pairs in duplex 6-2 would be negligibly affected for G(syn)-J(anti) (4d) or even stabilized by eliminating an unfavorable steric interaction at N$_2$ on G in the unlikely G(anti)-J(syn) pair (4e).

Figure 5:
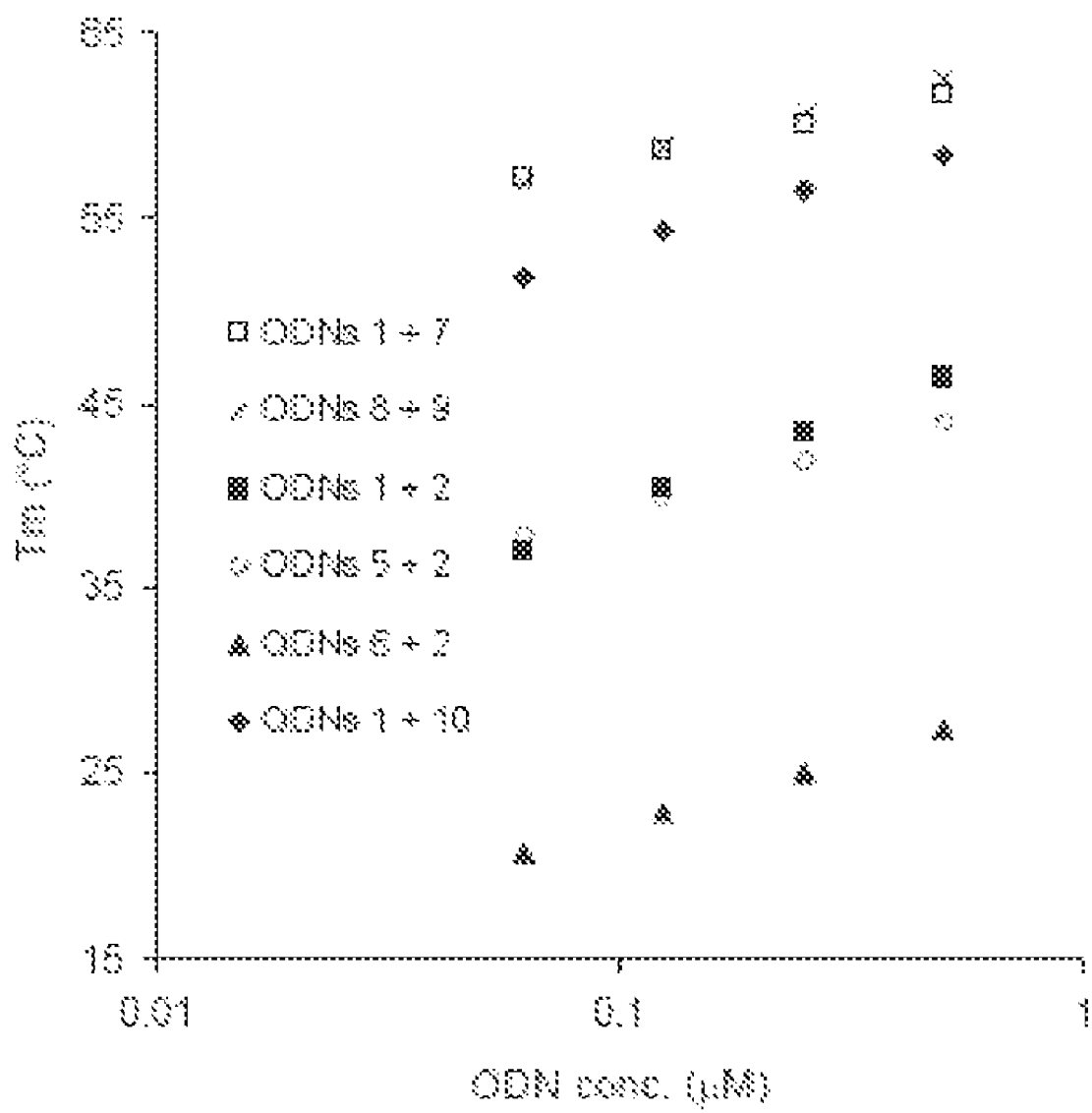
FIG. 5 is a plot of measured melting temperatures (Tm) for particular oligonucleotide mixtures. Tm values were determined by monitoring fluorescence of equimolar pairs of oligonucleotides plotted against the log concentration of each strand. The data shows that duplexes with matching HA pairs and GJ pairs results in purine-purine oligonucleotide structures with Watson-Crick interactions.

Obtaining significantly lower melting temperatures ($T_m$s, temperatures at which 50% strand dissociation occurs) for duplex 5-2 than for duplex 1-2 under identical conditions would imply anti-syn H•A association in duplex 1-2. Obtaining significantly lower $T_m$s for duplex 6-2 than for duplex 1-2 would imply anti-anti G•J association in duplex 1-2. $T_m$s observed for duplex 5-2 were quite similar to those of duplex 1-2, while duplex 6-2 was clearly destabilized relative to duplex 1-2, suggesting that Watson-Crick interactions existed in duplex 1-2 (FIG. 5).

Figure 6:
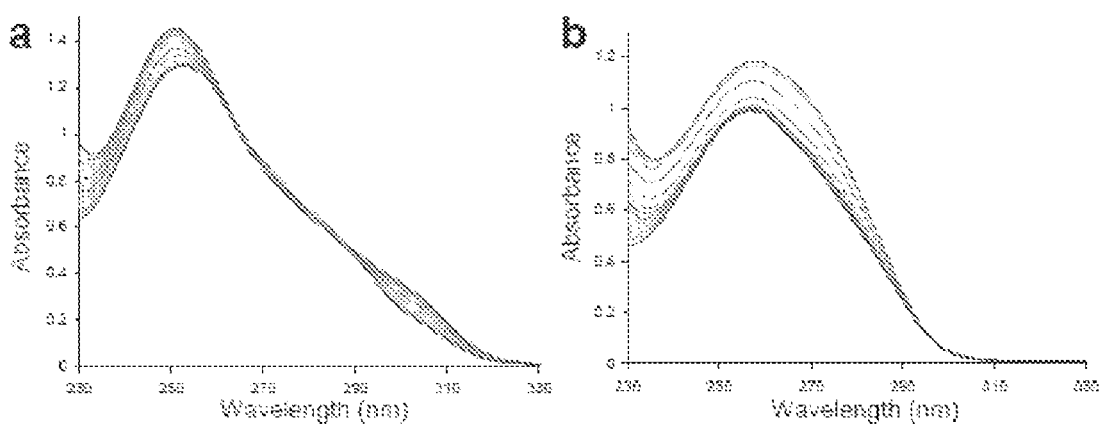
FIG. 6a is a plot of overlaid absorbance spectra of purine-purine duplex 4-2 varied with temperature
FIG. 6b is a plot of overlaid absorbance spectra of purine-purine duplex 11-9 also varied with temperature. The plots support a shift in tautomeric composition of J to N1-H.
Figure 7:
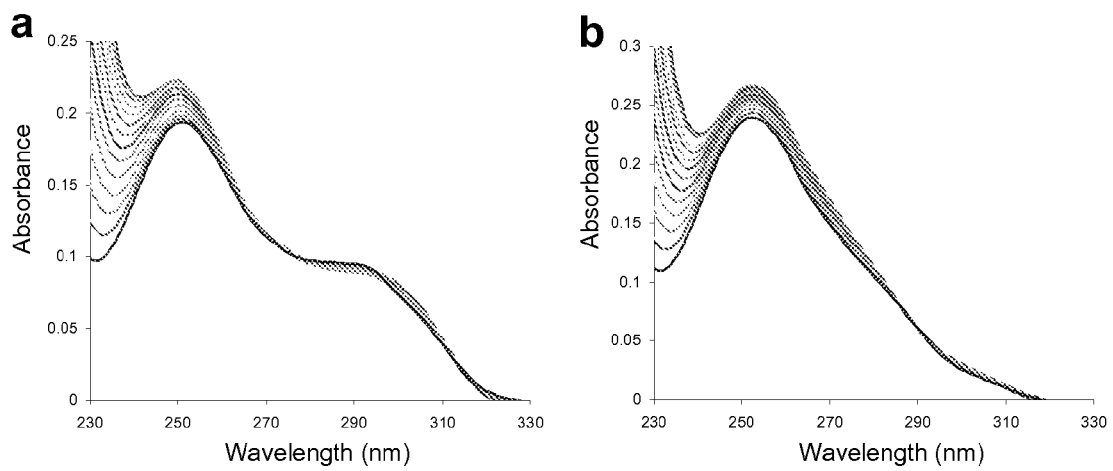
FIG. 7a is a plot of absorbance of oligodeoxynucleotide 2 at 5° C. increments.
FIG. 7b is a plot of absorbance of oligodeoxynucleotide 4 at 5° C. increments. The plotted data supports the presence of a tautomer of J at lower temperatures that shifts to the N1-H with increasing temperature.

Changes in absorbance spectra of duplex 4-2 with temperature reveal a shift in the tautomeric composition of constituent J nucleobases that further supports Watson-Crick association. The $N_1$—H tautomer of J has a characteristic UV maximum near 295 nm, while the $N_3$—H tautomer of J required for Watson-Crick association with G absorbs somewhat less in this region. Absorbance profiles of duplex 4-2 at 280 to 310 nm indicate that J shifts substantially to the $N_1$—H tautomer with increasing temperature (FIG. 6). Absorbance profiles of individual oligodeoxyribonucleotides 4 or 2 display lesser tautomeric shifts under identical conditions (FIG. 7). Conversely, absorbance profiles of duplexes associating through purine-pyrimidine interaction with J opposite 5-methylisocytosine (F), a Watson-Crick complement of the $N_1$—H tautomer of J, show a decrease in $N_1$—H tautomer as the duplexes dissociate with increasing temperature (FIG. 8a).

Figure 8:
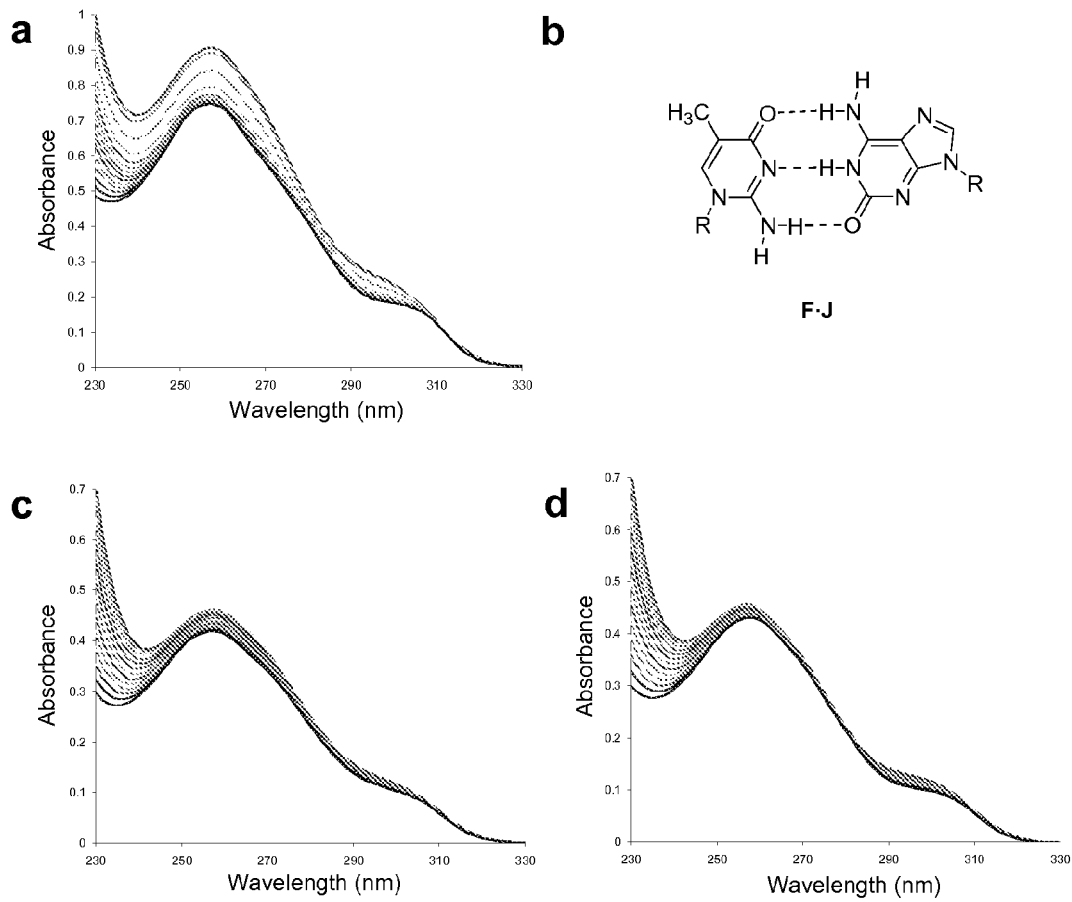
FIG. 8a is a plot of low temperature absorbance profiles of oligodeoxyribonucleotides 5'-AFJ AFT TTJ TJF G-3' (SEQ ID NO: 1) and 3'-TJF TJA AAF AFJ C-5' (SEQ ID NO: 2) indicating predominantly N1-H tautomer of J.
FIG. 8b is a depiction of a J-F pair associating through purine-pyrimidine interaction.
FIG. 8c is an absorbance profile of oligodeoxynucleotide 5'-AFJ AFT TTJ TJF G-3' (SEQ ID NO: 3).
FIG. 8d is an absorbance profile of oligodeoxynucleotide 3'-TJF TJA AAF AFJ C-5' (SEQ ID NO: 4).

The formation of duplex 4-2 is supported by the observed changes in the absorbance spectra and imply that while J in duplexes adopts the $N_1$—H tautomer opposite F as depicted in FIG. 8b, it adopts the $N_3$—H tautomer opposite G. A mixture of $N_1$—H and $N_3$—H tautomers of J can exist in single strand oligodeoxyribonucleotides in solution with tautomeric composition depending on sequence and temperature.

The association of duplex 1-2 was weaker than that of comparable duplexes formed through canonical purine-pyrimidine interaction. Additional oligodeoxyribonucleotides 7, 8, and 9 were used to create two control duplexes associating through Watson-Crick purine-pyrimidine interaction. All-pyrimidine oligonucleotides 7 and 1 can form duplex 1-7. In duplex 8-9, A•H and G•J pairs of duplex 1-2 were changed to A•T and G•C pairs, respectively, giving a canonical duplex with identical interstrand hydrogen bonding patterns. $T_m$s were substantially lower for duplex 1-2 than for the two control duplexes (FIG. 5). Chimeric duplex 1-10, associating through 8 consecutive purine-pyrimidine pairs and 6 consecutive purine-purine pairs had intermediate stability (FIG. 5). Accommodation of the purine-purine structure in this chimeric duplex without excessive destabilization shows that the structure of the purine-purine portion is not very different from a canonical duplex.

Figure 9:
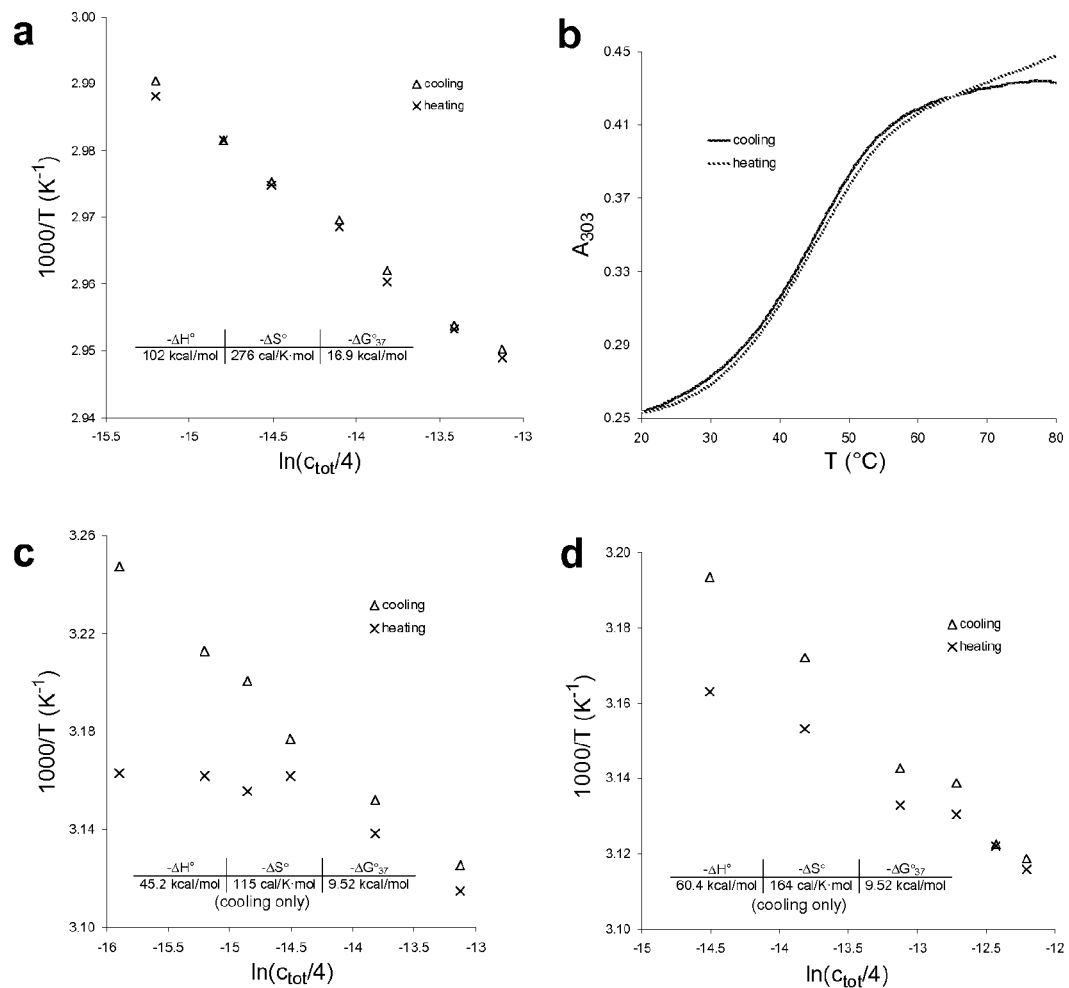
FIG. 9a is a Van't Hoff plot and thermodynamic parameters calculated from the plot, which is derived from melting temperatures from heating or cooling curves of duplex 11-9.
FIG. 9b is a plot of heating and cooling transitions of duplex 4-2.
FIG. 9c is a Van't Hoff plot and thermodynamic parameters calculated from the plot, which is derived from cooling curves monitoring absorbance at 248 nm of duplex 11-9.
FIG. 9d is a Van't Hoff plot and thermodynamic parameters calculated from the plot, which is derived from cooling curves monitoring absorbance at 303 nm of duplex 11-9.

Thermodynamic parameters were estimated for association of purine-purine duplex 4-2 and for association of control canonical duplex 11-9, an unlabeled analogue of duplex 8-9. A $\Delta G°_{37}$ of −16.9 kcal/mol for association of duplex 11-9 was determined from a Van't Hoff plot of $T_m$s at 260 nm (FIG. 9a). Although changes in absorbance of 4-2 upon dissociation arise at least partially from a shift in the tautomeric distribution of J, the changes are triggered by duplex dissociation, which mimics the hyperchromicity observed with canonical duplexes. Therefore, $\Delta G°_{37}$ of duplex 1-2 association was roughly estimated as −10 kcal/mol by measuring $T_m$s at 248 and 303 nm (FIGS. 9b, 9c, and 9d).

Figure 10:
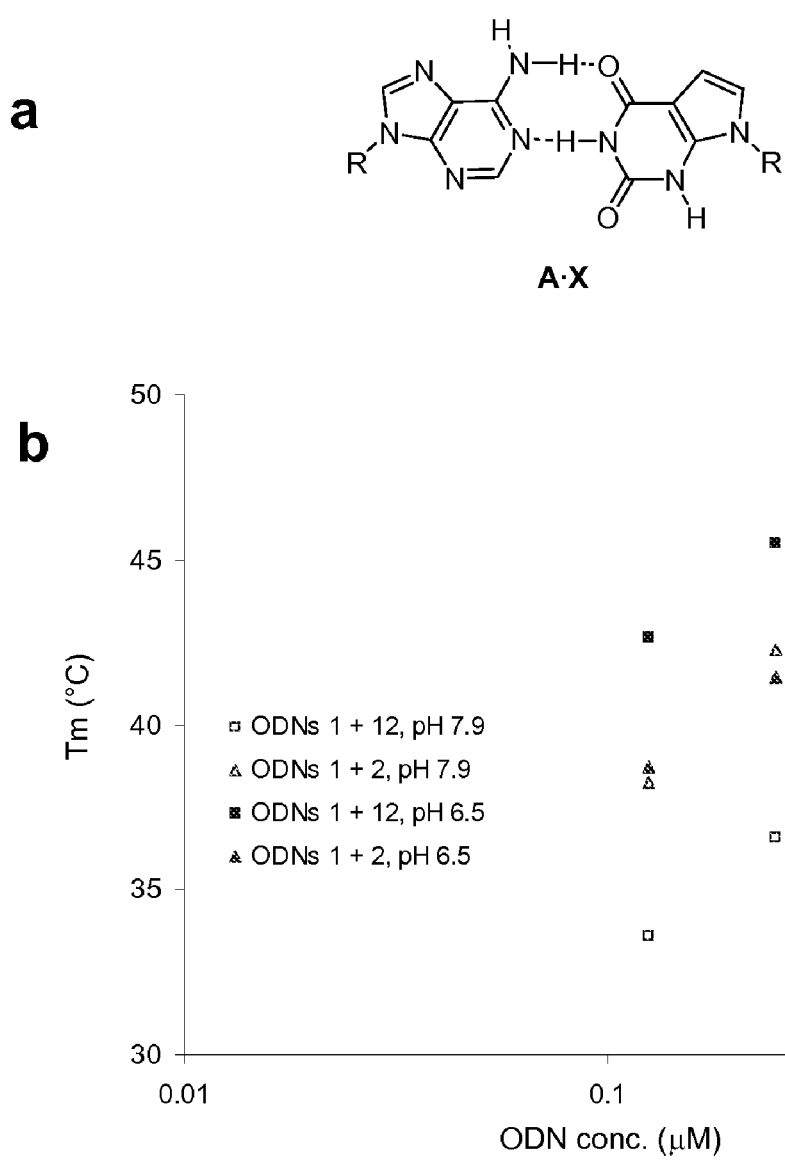
FIG. 10a depicts the association of a duplex pairing of 7-deazaxanthine (X) opposite adenine (A).
FIG. 10b is a plot of melting temperature at various concentrations of mixtures of oligodeoxynucleotides, also at various pH values, where the four hypoxanthine positions in oligodeoxynucleotide 2 were changed to 7-deazaxanthine.

In contrast to purine-purine duplexes, the association of "xDNA" duplexes with a $C_1$-$C_1'$ distance of ~13 Å and a natural deoxyribose-phosphate backbone, is usually more favorable than association of corresponding DNA duplexes. It is not immediately evident why xDNA duplexes and the purine-purine duplexes, with presumed similar $C_1$-$C_1'$ separation, have such a large difference in association. Without wishing to be bound to any one particular theory, a possible explanation is that nucleobases opposite adenine in the purine-purine duplexes do not position a carbonyl opposite $C_2$ of A. The absence of a carbonyl in this position could destabilize duplexes by disrupting hydration or by removing a favorable electrostatic interaction between an electronegative carbonyl oxygen and a partial positive charge at the edge of the opposing heterocycle. Duplex denaturation experiments introducing several "missing" carbonyls opposite adenine in duplex 1-12 with 7-deazaxanthosine demonstrated a stabilizing effect of the carbonyl (FIG. 10), but the magnitude of the effect appears insufficient to account for the difference in association between duplex 1-2 and 8-9. An additional difference is the relative orientation of the bonds between nucleobase and $C_1'$, which may also destabilize purine-purine duplexes relative to xDNA.

The purine-purine duplexes demonstrate that pyrimidine nucleobases are not required for sequence-specific formation of a deoxyribose duplex, a structure vital to replication of nucleic acids. This is the first demonstration of mixed sequence nucleic acids with a natural backbone and natural nucleobases associating in an alternative duplex structure. The sequence-specific recognition displayed by these structures makes the duplexes suitable in principle for information storage and replication through a base pairing mechanism analogous to the genetic system.

Figure 11:
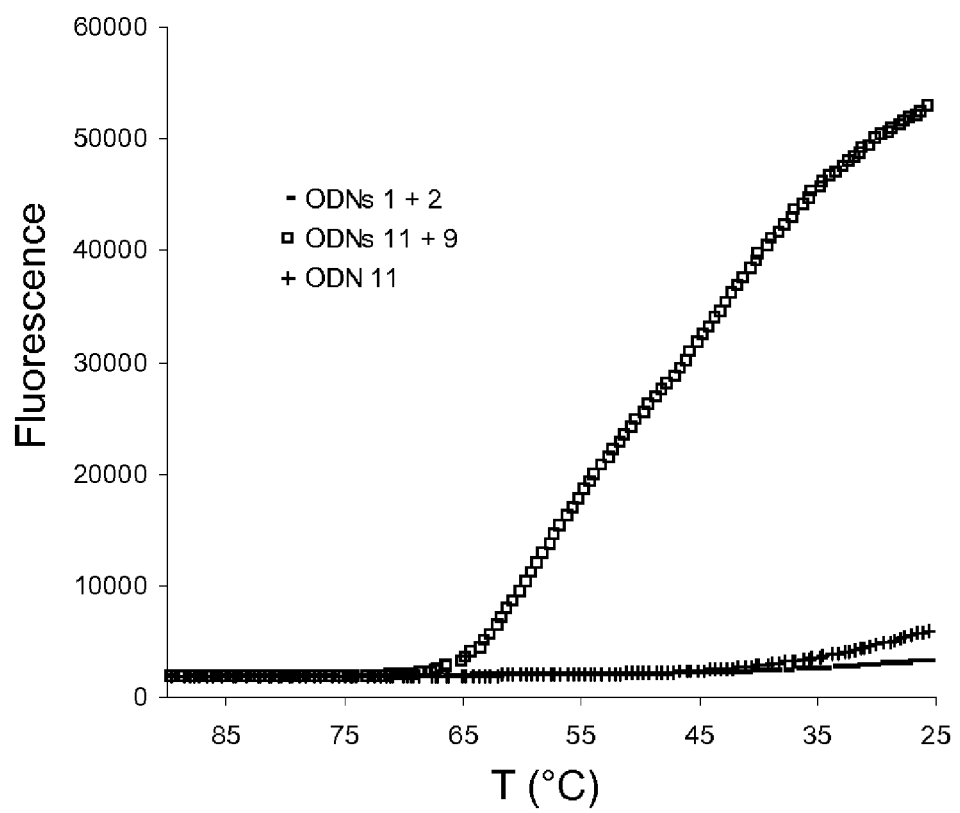
FIG. 11 is a plot of observed fluorescence at various temperatures for oligodeoxynucleotides 1 and 2 together, 11 and 9 together, and 11 by itself, all in the presence of a fluorescence dye.

Purine-purine duplexes will have novel properties and should have useful technological applications. Natural nucleic acid sequences containing poly-purine regions can be targeted with probes forming purine-purine or chimeric purine-purine/purine-pyrimidine interactions. Purine-purine nucleic acids can form duplex structures that will not act as substrate in enzymatically-mediated processes, such as polymerase replication, ligation, restriction, and mismatch repair. Small molecules, such as SYBR® Green I dye, used to target duplex nucleic acids will also exhibit changed interaction with purine-purine duplexes (FIG. 11).

It is to be understood that the foregoing descriptions of embodiments of the present invention are exemplary and explanatory only, are not restrictive of the invention, as claimed, and merely illustrate various embodiments of the invention. It will be appreciated that other particular embodiments consistent with the principles described in the specification but not expressly disclosed may fall within the scope of the claims.

---

What is claimed is:

1. A method comprising:
providing a heteropolynucleotide template comprising a region having a plurality of purine nucleotides coupled to a backbone of ribose or deoxyribose, and phosphate;
hybridizing to the heteropolynucleotide template an oligonucleotide molecule comprising a plurality of purine nucleotides coupled to a backbone of ribose or deoxyribose, and phosphate,
wherein a plurality of the purine nucleotides of the oligonucleotide molecule hybridize to purine nucleotides of the heteropolynucleotide template by forming complementary Watson-Crick interactions, thereby forming a stable anti-parallel duplex having a plurality of purine-purine nucleobase dyads.

2. The method according to claim 1, wherein the ribose or deoxyribose is selected from D-ribose and 2'-deoxy-D-ribose.

3. The method according to claim 1, wherein at least one purine-purine nucleobase dyad comprises a purine that adopts a tautomer that is not the major species of the nucleobase present in aqueous solution in the absence of this interaction.

4. The method according to claim 1, wherein both purines of at least one purine-purine nucleobase dyad adopt a tautomer that is not the major species of the nucleobase present in aqueous solution in the absence of this interaction.

5. The method according to claim 1, wherein the purine-purine nucleobase dyads are selected from the following:

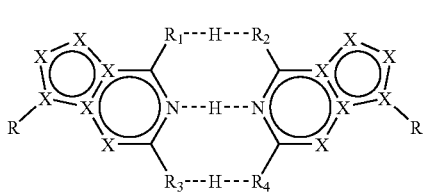

(1)

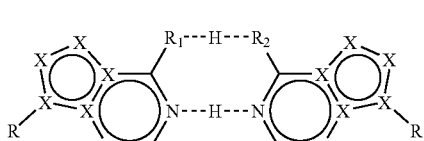

(2)

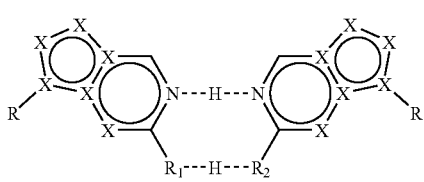

(3)

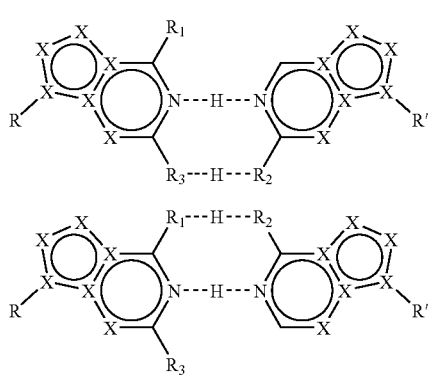

wherein X is independently selected from the group consisting of C, N, CH, and NH, provided that aromaticity is preserved;

each R and R' is selected from the group consisting of ribose and deoxyribose; and each $R_1$, $R_2$, $R_3$, and $R_4$ is selected from the group consisting of hydrogen bond donors —$NH_2$, —SH, and —OH, or the group of hydrogen bond acceptors =O, =S, =NH, —OH, —SH, and —$NH_2$, such that an individual hydrogen atom within a hydrogen bond (denoted —H—) is associated with one donor and one acceptor.

6. The method according to claim 1, wherein a plurality of the purine-purine nucleobase dyads have a hydrogen bond donor:acceptor pattern selected from the following patterns which are depicted using the nomenclature of Benner:

| | | |
|---|---|---|
| puADD-puDAA | puAD_-puDAA | puAD_-puDA_ |
| puAAD-puDDA | puAA_-puDDA | puAA_-puDD_ |
| puADA-puDAD | puADA-pu_AD | pu_DA-pu_AD |
| | puADD-pu_AA | pu_DD-pu_AA |
| | puAAD-pu_DA | pu_AD-pu_DA |
| | puADA-puDA_ | puAD_-puDA_ |

7. The method according to claim 1, wherein one or more purine-purine nucleobase dyad consists of:
(a) a first purine selected from adenine, 7-deazaadenine, or 3-deazaadenine and
(b) a second purine selected from hypoxanthine, 7-deazahypoxanthine, 3-deazahypoxanthine, 7-deazaxanthine, or xanthine.

8. The method according to claim 1, wherein one or more purine-purine nucleobase dyad consists of (a) a first purine selected from guanine, 7-deazaguanine, or 3-deazaguanine and (b) a second purine which is isoguanine 9. The method according to claim 1, wherein a plurality of purine-purine nucleobase dyads are contiguous.

10. The method according to claim 1, wherein the duplex comprises at least 3 contiguous purine-purine nucleobase dyads.

11. The method according to claim 1, wherein the duplex comprises at least 4 contiguous purine-purine nucleobase dyads.

12. The method according to claim 1, wherein the duplex comprises 5 or more contiguous purine-purine nucleobase dyads.

13. The method according to claim 1, wherein the duplex further comprises a plurality of complementary purine-pyrimidine nucleobase dyads.

14. The method according to claim 1, wherein the duplex further comprises a detectable label bound to at least one of the nucleobases.

15. The method according to claim 14, wherein the detectable label is a fluorophore.

16. The method according to claim 14, wherein the duplex further comprises a quencher.

17. The method according to claim 1, wherein the plurality of purine nucleotides of the heteropolynucleotide template are contiguous, and wherein the stable anti-parallel duplex formed by the hybridization of the oligonucleotide molecule to the heteropolynucleotide template has a plurality of contiguous purine-purine nucleobase dyads.

18. The method according to claim 1, wherein the oligonucleotide molecule consists essentially of purine nucleotides.

19. The method according to claim 1, wherein the region of the heteropolynucleotide template having the plurality of purine nucleotides includes purine nucleotides characterized by polymorphic variations; and a plurality of the purine nucleotides of the oligonucleotide molecule hybridize to purine nucleotides of the heteropolynucleotide template having one of the polymorphic variations.

* * * * *